(12) United States Patent
Mitsuhashi

(10) Patent No.: US 7,968,288 B1
(45) Date of Patent: Jun. 28, 2011

(54) DEVICE AND METHOD FOR HIGH-THROUGHPUT QUANTIFICATION OF MRNA FROM WHOLE BLOOD

(75) Inventor: Masato Mitsuhashi, Irvine, CA (US)

(73) Assignees: Hitachi Chemical Co., Ltd., Tokyo (JP); Hitachi Chemical Research Center, Irvine, CA (US)

(*) Notice: Subject to any disclaimer, the term of this patent is extended or adjusted under 35 U.S.C. 154(b) by 829 days.

(21) Appl. No.: 11/525,515

(22) Filed: Sep. 22, 2006

Related U.S. Application Data

(63) Continuation of application No. 10/796,298, filed on Mar. 9, 2004, which is a continuation-in-part of application No. 10/698,967, filed on Oct. 30, 2003, now abandoned, which is a continuation-in-part of application No. PCT/US03/12895, filed on Apr. 24, 2003.

(60) Provisional application No. 60/375,472, filed on Apr. 24, 2002.

(51) Int. Cl.
*C12Q 1/68* (2006.01)
*C12P 19/34* (2006.01)
*C12M 1/34* (2006.01)
*C07H 21/02* (2006.01)
*C07H 21/04* (2006.01)

(52) U.S. Cl. ....... 435/6; 435/91.1; 435/91.2; 435/91.51; 435/287.2; 536/23.1; 536/24.3; 536/24.33

(58) Field of Classification Search ............ 435/6, 91.1, 435/91.2, 91.51, 183, 287.2; 436/94; 536/23.1, 536/24.3, 24.33
See application file for complete search history.

(56) References Cited

U.S. PATENT DOCUMENTS

| | | | |
|---|---|---|---|
| 4,193,980 A * | 3/1980 | Clason et al. | 435/40.51 |
| 4,652,525 A * | 3/1987 | Rutter et al. | 435/252.33 |
| 4,923,620 A | 5/1990 | Pall | |
| 5,045,449 A * | 9/1991 | Ala-Kokko et al. | 435/6 |
| 5,175,109 A | 12/1992 | Sakata et al. | |
| 5,177,085 A | 1/1993 | Naef | |
| 5,707,526 A | 1/1998 | Kraus et al. | |
| 5,976,797 A | 11/1999 | Mitsuhashi | |
| 6,042,859 A * | 3/2000 | Shaklai | 426/264 |
| 6,136,555 A | 10/2000 | Jones | |
| 6,265,229 B1 | 7/2001 | Fodstad et al. | |
| 6,268,121 B1 | 7/2001 | Takeshita et al. | |
| 6,300,058 B1 | 10/2001 | Akitaya et al. | |
| 6,511,830 B1 | 1/2003 | Takahashi et al. | |
| 6,617,170 B2 | 9/2003 | Augello et al. | |

(Continued)

FOREIGN PATENT DOCUMENTS

EP 1138780 A1 10/2001

(Continued)

OTHER PUBLICATIONS

The definition of "Guanidine" from Wikipedia, the free encyclopedia. Printed on Sep. 28, 2009.*

(Continued)

*Primary Examiner* — Frank W Lu
(74) *Attorney, Agent, or Firm* — Knobbe, Martens, Olson & Bear LLP

(57) ABSTRACT

Disclosed are a method, device kit, and automated system for simple, reproducible, and high-throughput quantification of mRNA from whole blood. More particularly, the method, device, kit and automated system involve combinations of leukocyte filters attached to oligo(dT)-immobilized multi-well plates.

14 Claims, 33 Drawing Sheets

Optimal guanidine thiocyanate concentration.

U.S. PATENT DOCUMENTS

| | | | |
|---|---|---|---|
| 6,846,642 B2 * | 1/2005 | Mok et al. | 435/7.23 |
| 7,745,180 B2 | 6/2010 | Mitsuhashi | |
| 2003/0157550 A1 | 8/2003 | Mitsuhashi | |
| 2003/0170669 A1 | 9/2003 | Garvin | |
| 2005/0059024 A1 * | 3/2005 | Conrad | 435/6 |

FOREIGN PATENT DOCUMENTS

| | | |
|---|---|---|
| WO | WO 99/32654 | 7/1999 |
| WO | WO 00/21973 | 4/2000 |
| WO | WO 00/77253 | 12/2000 |
| WO | WO 02/14560 | 2/2002 |
| WO | WO 03/062462 | 7/2003 |

OTHER PUBLICATIONS

Maniatis et al., Molecular Cloning: A Laboratory Manual, pp. 191-193, 1982. Published by Cold Spring Harbor Laboratory, Box 100, Cold Spring Harbor Laboratory, New York.*

Isolation and Analysis of Nucleic Acids from Human Blood: A Moleculear diagostics Application. Promega Notes, 72, 13-14, 1999.*

Kephart, Rapid Isolation of RNA from Small Quantities of Human Whole Blood for Use in RT-PCR Analysis. Promega Notes, 62, 11, 1997.*

Donald et al., Isolating RNA from whole blood- the dawn of RNA-based diagnosis? Nature, 362, 186-188, 1993.*

Rainer I., et al. "Improved efficiency for single-sided PCR by creating a reusable pool of first-strand cDNA coupled to a solid phase," *Nucleic Acids Research*, vol. 19, No. 14, 1991, p. 4010.

Tominaga K., et al. "Colorimetric ELISA measurement of specific mRNA on immobilized-oligonucleotide-coated microtiter plates by reverse transcription with biotinylated mononucleotides," *Clinical Chemistry*, vol. 42, No. 11, 1996, pp. 1750-1757.

Vlems F.A., et al. "Reliability of quantitative reverse-transcriptase-PCR-based detection of tumour cells in the blood between different laboratories using a standardised protocol," *European Journal of Cancer*, vol. 39, No. 3, 2003, pp. 388-396.

Qiagen, RNeasy MinElute Cleanup Handbook, 2003, pp. 1-30.

"Fluorometric determination of total mRNA with oligo(dt) immobilized on microtiter plates", Miura Y. et al., Clinical Chemistry, vol. 42, No. 11, 1996, pp. 1758-1764.

"Construction of cDNA bank from biopsy specimens for multiple gene analysis of cancer", Ishikawa T. et al., Clinical Chemistry, vol. 43, No. 5, 1997, pp. 764-770.

"Rapid, stable ambient storage of leukocyte RNA from whole blood", Yoshimasa Aso, et al., Clinical Chemistry, vol. 44, No. 8, 1998.

Patent Abstract of Japan, vol. 015, No. 068, corresponding to JP 02295485.

Supplementary European Search Report for European Patent Application No. EP 03 72 4238, issued May 17, 2005.

PCT Invitation to Pay Additional Fees for International Application No. PCT/US2004/036309, issued May 30, 2005.

Melanoma Research, Analysis of melanoma cells in peripheral blood by reverse transcription-polymerase chain reaction for tyrosinase and Mart—1 after mononuclear cell collection with cell preparation tubes: a comparison with the whole blood guanidinium isothiocyanate RNA isolation method, vol. 10 (2000), 119-126, T.J. de Vries, A. Fourkour, C.J.A. Punt, D.J. Ruiter and G.N.P. van Muijen.

Proceedings of the National Academy of Sciences of the United States of America, Diagnosis of Chronic Myeloid and Acute Lymphocytic Leukemias by Detection of Leukemia-Specific mRNA Sequences Amplified in vitro, vol. 85, No. 15 (Aug. 1, 1988), 5698-5702, Ernest S. Kawasaki, Steven S. Clark, Mazie Y. Coyne, Stephen D. Smith, Richard Champlin, Owen N. Witte, Frank P. McCormick.

Clinical Chemistry, Direct reverse transcription-PCR on oligo (dT)-immobilized polypropylene microplates after capturing total mRNA from crude cell lysates, 44:11 (Nov. 1, 1998), 2256-2263, Yohei Hamaguchi, Yoshimasa Aso, Hiroshi Shimada, and Masato Mitsuhashi.

Clinical Chemistry, Quantitative Analysis of Tyrosinase Transcripts in Blood, 46:7 (Jul. 1, 200), 921-927, Malin Johansson, Eva K. Pisa, Vuokko Tormanen, Kerstin Arstrand, Bertil Kagedal.

British Journal of Haematology, Expression of bcr-abl mRNA in individual chronic myelogenous leukaemia cells as determined by in situ amplification, 112 (Mar. 1, 2001), 749-759, Katharina Pachmann, Shourong Zhao, Thomas Schenk, Hagop Kantarjian, Adel K. El-Naggar, Michael J. Siciliano, Jie-Qiang Guo, Ralph B. Arlingilaus and Michael Andreeff.

Clinical Chemistry, Quantitative Reverse Transcription-PCR Measurement of Thyroglobulin mRNA in Peripheral Blood of Healthy Subjects, 45:6 (Jun. 1, 1999), 785-789, Susan T. Wingo, Matthew D. Ringel, Jeffrey S. Anderson, Aneeta D. Patel, Yvonne D. Lukes, Yin-Ying Djuh, Barbara Solomon, Diamaud Nicholson, Pina L. Balducci-Silano, Michael A. Levine, Gary L. Francis, R. Michael Tuttle.

Clinical Chemistry, Molecular and immunological detection of circulating tumor cells and micrometastases from solid tumors, 42:9 (Sep. 1996), 1369-1381, Timothy J. Pelkey, Henry F. Frierson Jr., David E. Bruns.

Journal of Clinical Microbiology, Ultrasensitive Reverse Transcription-PCR Assay for Quantitation of Human Immunodeficiency Virus Type 1 RNA in Plasma, (Oct. 1998), 2964-2969, Rita Sun, Joanne Ku, Harsha Jayakar, Jo-Chi Kuo, Donald Brajmbilla, Steven Herman, Maurice Rosenstraus, Joanne Spadoro.

RNAture Reagents for mRNA Isolation, Buffers, <Apr. 24, 2002, at http://mature.com/product_reagents.htm.

RNAture GenePlate® 96-well mRNA Isolation Kit, GenePlate®, <Apr. 24, 2002, at http://mature.com/product_geneplate.htm.

Pall Corporation, Pall Leukosorb® Medium, Fibrous Medium, <Apr. 24, 2002, at http://www.pall.com/20610_4785.asp.

Amplicor HIV-1 Monitor Test—Standard Method, Aug. 1, 2000.

Khomyakova et al., On-chip hybridization kinetics for optimization of gene expression experiments, BioTechniques, Jan. 2008, vol. 44, Issue 1, pp. 109-117.

Promega Overnight Protocol, T4 DNA Ligase Blue/White Cloning Part# 9PIM180; http://promega.com/tbs/9pim180/9pim180.pdf, Promega Corporation, USA, Jan. 2007.

Sambrook et al., Molecular cloning: a laboratory manual, Cold Spring Harbor Laboratory Press, 2001, vol. Third Edition, p. 15.16.

Schwarz et al., Plasmid-mediated Chloramphenicol Resistance in *Staphylococcus hyicus*, Journal of General Microbiology, 1989, vol. 135, pp. 3329-3336.

* cited by examiner

Efficiency of leukocyte trapping of fresh and frozen blood samples on filterplates cDNA synthesis from both specific antisense primer (NNN) and immobilized oligo(dT).

Recovery of specifically primed RNA with and without denaturization.

mRNA quantification scheme using control RNA.

PCR cycles.

PCR cycles.

Performance of Control RNA.

FIG. 20A Spiked standard RNA(molecules per well)

Spiked standard RNA(molecules per well)

Recovery of RNA among various subjects

DEVICE AND METHOD FOR HIGH-THROUGHPUT QUANTIFICATION OF MRNA FROM WHOLE BLOOD

RELATED APPLICATIONS

This application is a continuation of U.S. application Ser. No. 10/796,298 filed on Mar. 9, 2004, now U.S. Pat. No. 7,745,180 B2, which is a continuation-in-part of U.S. application Ser. No. 10/698,967, filed on Oct. 30, 2003, now abandoned, which is a continuation-in-part of International Application No. PCTUS03/12895, which was filed in English on Apr. 24, 2003, and was published in English, and claims the benefit of U.S. Provisional Application No. 60/375,472, filed on Apr. 24, 2002.

BACKGROUND OF THE INVENTION

1. Field of the Invention

The present invention relates to high-throughput isolation and quantification of mRNA from whole blood. More particularly, this invention relates to a method and device for isolating and amplifying mRNA using combinations of leukocyte filters attached to oligo(dT)-immobilized multi-well plates.

2. Description of the Related Art

Research in the field of molecular biology has revealed that the genetic origin and functional activity of a cell can be deduced from the study of its ribonucleic acid (RNA). This information may be of use in clinical practice, to diagnose infections, to detect the presence of cells expressing oncogenes, to detect familial disorders, to monitor the state of host defense mechanisms and to determine the HLA type or other marker of identity. RNA exists in three functionally different forms: ribosomal RNA (rRNA), transfer RNA (tRNA) and messenger RNA (mRNA). Whereas stable rRNA and tRNA are involved in catalytic processes in translation, mRNA molecules carry genetic information. Only about 1-5% of the total RNA consists of mRNA, about 15% of tRNA and about 80% of rRNA.

mRNA is an important diagnostic tool, particularly when it is used to quantitatively observe up- or down-regulation of genes. Human peripheral blood is an excellent clinical resource for mRNA analysis. The detection of specific chimeric mRNA in blood, for example, indicates the presence of abnormal cells and is used in molecular diagnostics for chronic myelogenous leukemia (CML) (Kawasaki E. S., Clark S. S., Coyne M. Y., Smith S. D., Champlin R., Witte O. N., and McCormick F. P. 1988. Diagnosis of chronic myeloid and acute lymphocytic leukemias by detection of leukemia-specific mRNA sequences amplified in vitro. Proc. Natl. Acad. Sci. USA 85:5698-5702, Pachmann K., Zhao S., Schenk T., Kantarjian H., El-Naggar A. K., Siciliano M. J., Guo J. Q., Arlinghaus R. B., and Andreeff M. 2001. Expression of bcr-able mRNA individual chronic myelogenous leukaemia cells as determined by in situ amplification. Br. J. Haematol. 112:749-59). Micrometastatic cancer cells can also be detected in blood by measuring cancer-specific mRNA, such as carcinoembryonic antigen (CEA) for colon cancer, prostate specific antigen (PSA) for prostate cancer, thyroglobulin for thyroid cancer (Wingo S. T., Ringel M. D., Anderson J. S., Patel A. D., Lukes Y. D., Djuh Y. Y., Solomon B., Nicholson D., Balducci-Silano P. L., Levine M. A., Francis G. L., and Tuttle R. M. 1999. Quantitative reverse transcription-PCR measurement of thyroglobulin mRNA in peripheral blood of healthy subjects. Clin. Chem. 45:785-89), and tyrosinase for melanoma (Pelkey T. J., Frierson H. F. Jr., and Bruns D. E. 1996. Molecular and immunological detection of circulating tumor cells and micrometastasis from solid tumors. Clin. Chem. 42:1369-81). Moreover, as the levels of these cancer-specific mRNA can change following treatment, quantification of specific mRNA provides for a useful indicator during treatment follow-up.

As blood contains large quantities of non-nucleated erythrocytes (approximately 5 million cells/µL) compared to leukocytes (approximately 5000 leukocytes/µL), the isolation of granulocytes or lymphocytes from whole blood is commonly performed as the first step in mRNA analysis. However, due to inconsistencies in the recovery of specific subsets of leukocytes among different samples, the number of isolated leukocytes is determined for each sample and results are expressed as the quantity of mRNA per leukocytes, not mRNA/µL blood. Moreover, mRNA quantities may change during lengthy isolation processes. While no method exists for the isolation of cancer cells from blood, gene amplification technologies enable the identification and quantification of specific mRNA levels even from a pool of different genes, making whole blood an ideal material for mRNA analysis when gene-specific primers and probes are available.

The scientific community is facing a huge problem of institute-to-institute and experiment-to-experiment variation in gene expression analysis, because of the lack of standardization. Although recent gene amplification technologies provide an absolute quantity of template DNA, these values cannot be converted to the amounts of the gene in the original materials, due to the lack of information of the yield of RNA recovery and the efficiency of cDNA synthesis in each sample. Total RNA is frequently used as a standardization marker for mRNA quantitation, and results are typically expressed as the amounts of genes per µg total RNA. However, it must be emphasized that total RNA does not represent mRNA, because the fraction of mRNA is only 1-5% of total RNA, and mRNA volume varies even when the amounts of total RNA is identical. The yield of total RNA or mRNA also varies widely depending on which method is employed. Once RNA is extracted, the next step is the synthesis of cDNA, which itself can create uncertainty since existing methods do not indicate whether each RNA template creates a single copy of cDNA in each experiment. In order to avoid the above problems, relative quantitation is used widely by comparing the data of target genes to that of housekeeping genes or rRNA. However, the amounts of control genes are typically not consistent and may change during experiments. Moreover, this variation presents a serious problem for clinical diagnostics, since each clinical specimen is typically analyzed at a different point in time.

It is typically very difficult to isolate pure mRNA from whole blood because whole blood contains large amounts of RNAases (from granulocytes) and non-nucleated erythrocytes. Although various RNA extraction methods are available for whole blood applications (de Vries T. J., Fourkour A., Punt C. J., Ruiter D. J., and van Muijen G. N. 2000. Analysis of melanoma cells in peripheral blood by reverse transcription-polymerase chain reaction for tyrosinase and MART-1 after mononuclear cell collection with cell preparation tubes: a comparison with the whole blood guanidinium isothiocyanate RNA isolation method. Melanoma Research 10:119-26, Johansson M., Pisa E. K., Tormanen V., Arstrand K., and Kagedal Bl. 2000. Quantitative analysis of tyrosinase transcripts in blood. Clin. Chem. 46:921-27, Wingo S. T., Ringel M. D., Anderson J. S., Patel A. D., Lukes Y. D., Djuh Y. Y., Solomon B., Nicholson D., Balducci-Silano P. L., Levine M. A., Francis G. L., and Tuttle R. M. 1999. Quantitative reverse transcription-PCR measurement of thyroglobulin mRNA in peripheral blood of healthy subjects. Clin. Chem. 45:785-89), the assay procedures are labor-intensive, require several rounds of centrifugation, and involve careful handling that is essential in eliminating ribonuclease activities.

Consequently, there exists a need for a quick and easy method and device for isolating and quantifying large quantities of mRNA from whole blood. Specifically, there exists a need for a high throughput, whole blood-derived mRNA-processing technology with reproducible recovery and a seamless process to gene amplification.

SUMMARY OF THE INVENTION

The present invention discloses an efficient high throughput method and device for isolating and quantifying mRNA directly from whole blood, with reproducible recovery, using combinations of leukocyte filters attached to oligo(dT)-immobilized multi-well plates.

One aspect of the invention includes a method of high throughput quantification of mRNA in whole blood, including the steps of: (a) collecting whole blood; (b) removing erythrocytes and blood components from the whole blood by filtration to yield leukocytes on a filter membrane; (c) subjecting the leukocytes to cell lysis to produce a lysate containing mRNA; (d) transferring the lysate to an oligo(dT)-immobilized plate to capture the mRNA; and (e) quantifying the mRNA.

In one preferred embodiment of the method, an anticoagulant is administered to the whole blood prior to collection of leukocytes. Several filter membranes can be layered together to increase the yield of captured leukocytes. The leukocytes that are trapped on the filter membrane are lysed using a lysis buffer to release mRNA from the leukocytes. The transfer of lysate to the oligo(dT)-immobilized plate can be accomplished using centrifugation, vacuum aspiration, positive pressure, or washing with ethanol followed by vacuum aspiration. The mRNA is quantified by producing cDNA and amplifying the cDNA by PCR. Particularly preferred embodiments use TaqMan PCR to quantify mRNA.

Another aspect of the invention comprises the use of artificial control RNA as a universal standard. In preferred embodiments, measuring the recovery of the standard RNA in each sample allows the results of gene amplification to used to determine the amounts of mRNA present per µl of whole blood. Embodiments of the present result in low coefficients of variation between samples and experiments. In preferred embodiments, variation can be minimized during RNA recovery, cDNA synthesis, and quantification. The use of a standardized control RNA allows more efficient assays, quantification, and comparative testing.

Another aspect of the invention includes a device for performing high throughput quantification of mRNA in whole blood, wherein the device includes: (a) a multi-well plate containing: a plurality of sample-delivery wells; a leukocyte-capturing filter underneath the wells; and an mRNA capture zone underneath the filter which contains immobilized oligo (dT); and (b) a vacuum box adapted to receive the filter plate to create a seal between the plate and the box. In one preferred embodiment of the device, the leukocytes are captured on a plurality of filter membranes that are layered together. In another preferred embodiment of the device, the vacuum box is adapted to receive a source of vacuum. In another preferred embodiment of the device, a multi-well supporter is inserted between the vacuum box and the multi-well plates.

Another aspect of the invention includes a kit, which contains: the device for performing high throughput quantification of mRNA in whole blood, heparin, a hypotonic buffer, and a lysis buffer.

Another aspect of the invention includes a fully automated system for performing high throughput quantification of mRNA in whole blood, including: a robot to apply blood samples, hypotonic buffer, and lysis buffer to the device; an automated vacuum aspirator and centrifuge, and automated PCR machinery.

BRIEF DESCRIPTION OF THE DRAWINGS

FIG. 20A is a graph showing Ct values for spiked standard RNA.

FIG. 22A is a graph showing in vitro induction of mRNA in whole blood.

FIG. 22B is a graph showing blood storage before in vitro stimulation.

FIG. 22C is a graph showing in vitro induction of FasL mRNA among various subjects, by showing mRNA molecules/mL blood for both stimulation and vehicle control, respectively.

FIG. 22D is a graph showing in vitro induction of p21 mRNA among various subjects, by showing mRNA molecules/mL blood for both stimulation and vehicle control, respectively.

FIG. 22E is the same graph as FIG. 22C rotated until the regression line becomes horizontal.

FIG. 22F is the same graph as FIG. 22D rotated until the regression line becomes horizontal.

FIG. 22G graphs the same data as FIG. 22C, showing fold increase for individual subjects.

FIG. 22H graphs the same data as FIG. 22D, showing fold increase for individual subjects.

DETAILED DESCRIPTION OF THE PREFERRED EMBODIMENT

The present invention allows analysis of larger volumes of unprepared whole blood, provides an efficient means of analyzing mRNA that is derived exclusively from white blood cells; removes rRNA and tRNA, provides consistent mRNA recovery, and is easily adaptable to automation. The present invention provides a sensitive quantification system, including: absolute quantification using real time PCR, and excellent reproducibility with coefficients of variation ranging from 20-25%. Moreover, the present invention is applicable to various disease targets (Table I).

TABLE I

| Clinical targets | | |
|---|---|---|
| Stimulation | Diseases | Candidate Genes |
| (-) | Leukemia | Translocation gene |
|  | Cancer (diagnostics, monitoring, screening) | Cancer-specific gene from micrometastatic cancer cells |
|  | HIV/CMV (diagnostics, monitoring, blood bank) | Virus-derived mRNA from infected WBCs |
| In vivo sensitivity | Anti-leukemia drugs | Apoptosis |
|  | Immuno-suppressant | Cytokines |
|  | Side effect of anti-cancer drugs on WBCs | Housekeeping genes |
| In vitro | Anti-viral drug sensitivity | Virus-derived mRNA from infected WBCs |

Figure 1:
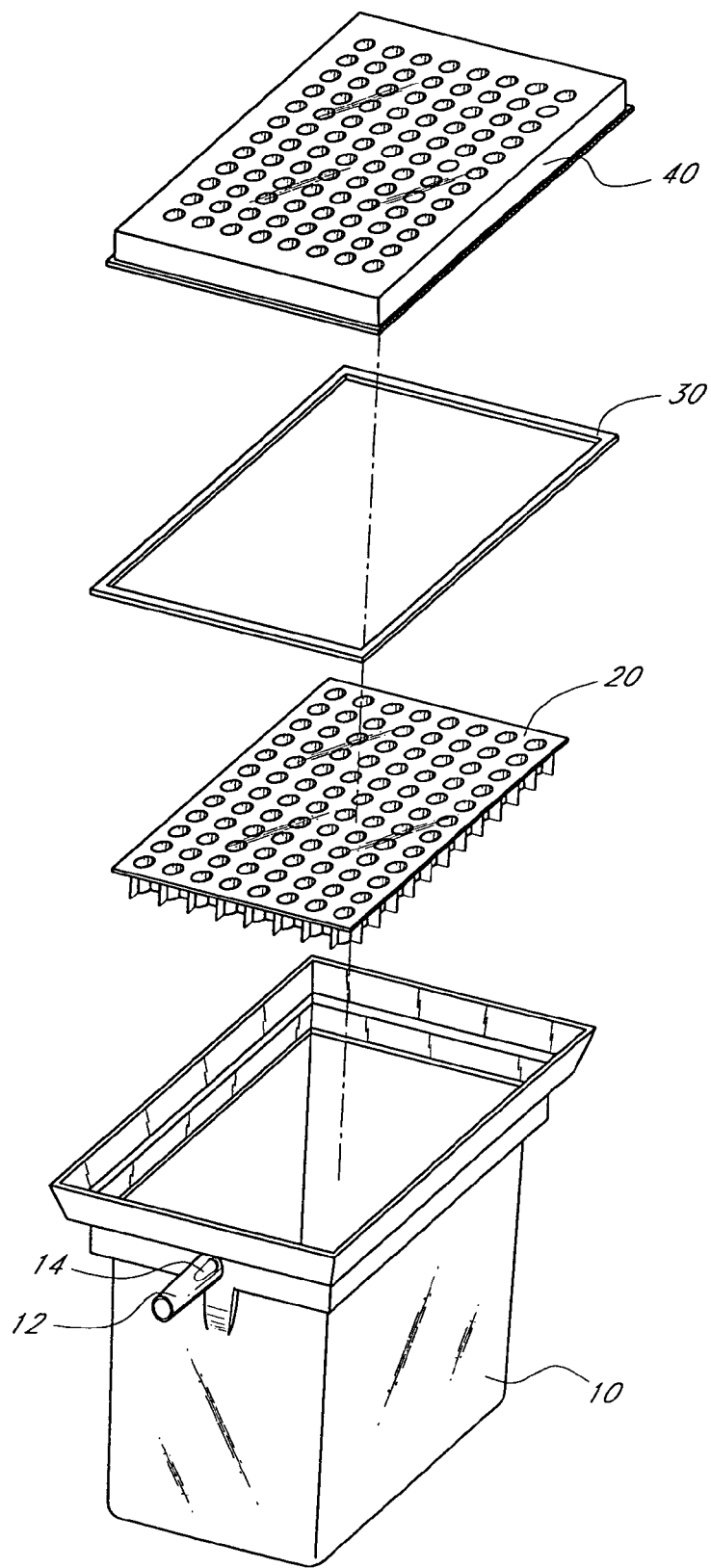
FIG. 1 is an exploded drawing of the high throughput mRNA device.
Figure 2:
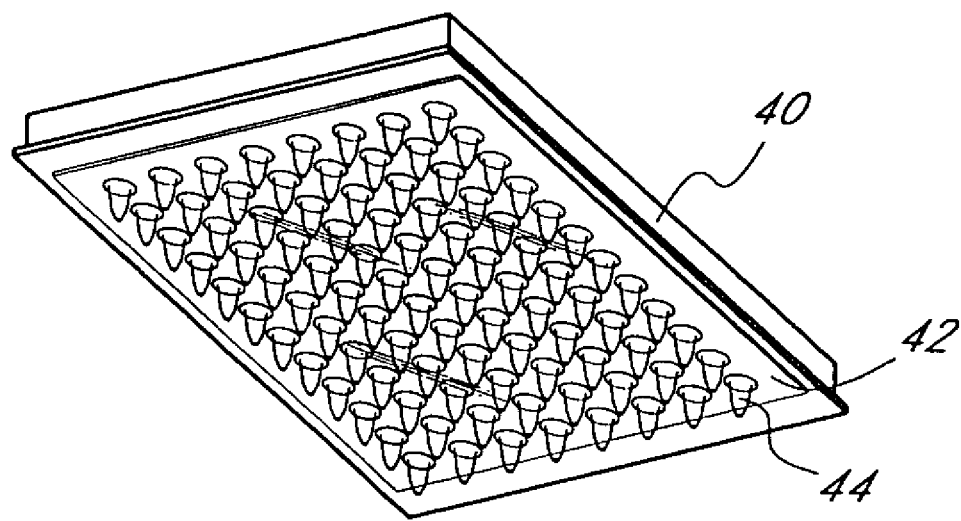
FIG. 2 depicts the multi-well plate, including the leukocyte filter and oligo-(dT)-immobilized filter wells, of the high throughput mRNA device.

The invention is not limited to any particular mechanical structure. However, FIGS. 1 and 2 show a preferred structure for implementing the high throughput mRNA quantification of the present invention. A vacuum box 10 forms the base of the structure. The vacuum box can be made of any material sufficiently strong to withstand vacuum aspiration; however, disposable plastic material is preferred. The vacuum box is adapted to receive a source of vacuum in order to perform vacuum aspiration 12. A filter plug 14 is located within the vacuum aspirator adapter of the vacuum box. The vacuum box 10 preferably has a ledge 16 to mate with a multi-well filter plate 40, or optionally, a multi-well supporter 20. The multi-well supporter 20 is optionally provided inside the upper part of the vacuum box so as to support the multi-well filterplate 40. A sealing gasket 30, preferably comprised of silicon-based rubber or other soft plastic, is located on top of the multi-well supporter. Above the sealing gasket lies the multi-well filter plate 40, which contains multiple sample wells 46, multiple leukocyte-capturing filters 42 underneath the sample-delivery wells, and an mRNA capture zone 44 under the filter. Oligo(dT)-immobilized is contained in the wells of the mRNA capture zone.

One preferred embodiment involves a simple, reproducible, and high throughput method of mRNA quantification from whole blood. The rapid protocol minimizes the secondary induction or degradation of mRNA after blood draw, and the use of 96-well filterplates and microplates allows the simultaneous manipulation of 96 samples. Minimal manipulation during the procedure provides for very small sample-to-sample variation, with coefficient of variation (CV) values of less than 30%, even when PCR is used as a means of quantification.

In one embodiment, the method involves preparation of the vacuum box. In one preferred embodiment, a blood encapsulator such as polyacrylate polymer matrix (Red Z, Safetec) is added to the vacuum box to solidify the blood. A multi-well supporter is then placed in the vacuum box. A sealing gasket made of silicon-based rubber or other soft plastics is then placed on top of the multi-well plate supporter. A filter plug (X-6953, 60µ Filter Plug HDPE, Porex Products Groups) is placed in the vacuum aspirator adapter of the vacuum box.

In this embodiment, the method involves the preparation of the filter plate. Either glassfiber membranes or leukocyte filter membranes can be used to capture leukocytes. In order to simplify the assay, multiple-well filterplates are constructed using glassfiber membranes or leukocyte filter membranes to enable the simultaneous processing of multiple blood specimens. Examples of filters for capturing leukocytes are disclosed in U.S. Pat. Nos. 4,925,572 and 4,880,548, the disclosures of which are hereby incorporated by reference. Adsorption of leukocytes on fiber surfaces is generally accepted as the mechanism of leukocyte removal. Since the surface area of a given weight of fibers is inversely proportional to the diameter of the fibers, it is to be expected that finer fibers will have higher capacity and that the quantity as measured by weight of fibers necessary to achieve a desired efficiently will be less if the fibers used are smaller in diameter. A number of commonly used fibers, including polyesters, polyamides, and acrylics, lend themselves to radiation grafting, as they have adequate resistance to degradation by γ-radiation at the levels required for grafting and are of a structure with which available monomers can react. PBT has been the principal resin used for the development of the products of this invention and is the resin used in the examples. It should be noted, however, that other resins may be found which can be fiberized and collected as mats or webs with fibers as small as 1.5 micrometers or less, and that such products, with their critical wetting surface tensions adjusted as necessary to the optimum range, may be well suited to the fabrication of equally efficient but still smaller leukocyte depletion devices. Similarly, glass fibers, appropriately treated, may be usable to make effective devices. Absorption of CD4 mRNA is up to four times as effective when using PBT-based filters as opposed to glass fiber-based filters. The filter plate is placed in the vacuum box. In another preferred embodiment, multiple filter membranes are layered together to increase the amount of leukocytes captured from whole blood. In one preferred embodiment, the filter plate is placed upon the plate supporter and the sealing gasket. In another preferred embodiment, the filter plate is sealed with a plastic adhesive tape (Bio-Rad 223-9444), and the tape is cut to allow access to a desired number of wells. In another preferred embodiment, each well to which a sample will be added is washed with a hypotonic buffer (200 µL 5 mM Tris, pH 7.4).

The method preferably involves collecting blood, adding the blood to the multi-well filter plate, and removal of erythrocytes and other non-leukocyte components. In one preferred embodiment, whole blood can be drawn into blood collection tubes containing anticoagulants, which increase the efficiency of the leukocyte filtering. The anticoagulant, heparin, is particularly effective in increasing the efficiency of leukocyte filtering. In one preferred embodiment, the blood sample can be frozen, which removes some of the RNAases that destroy mRNA. The wells can be washed with a hypotonic buffer. Once blood has been added to the desired number of wells on the filterplate, the blood is filtered through the filter membrane. Filtration can be affected through any technique known to those of skill in the art, such as centrifugation, vacuum aspiration, or positive pressure.

In one especially preferred embodiment, vacuum aspiration is commenced (with 6 cm Hg) after the blood samples have been added to the filterplate wells. Each well is washed several times with a hypotonic buffer (12× with 200 µL 5 mM Tris, pH 7.4). In another preferred embodiment, each well containing a sample is washed with ethanol (1× with 200 µL 100% ethanol), which dries the filter membrane and significantly increases the efficiency of leukocyte trapping during vacuum aspiration. In another preferred embodiment, the vacuum is then applied (20 cm Hg for >2 min).

The method involves cell lysis and hybridization of mRNA to the oligo(dT)-immobilized within the mRNA capture zone. Lysis buffer is applied to the filterplate wells (40 µL/well), and incubation is allowed to occur (room temperature for 20 min) to release mRNA from the trapped leukocytes. In one preferred embodiment, the multi-well filterplate is sealed in a plastic bag and centrifuged (IEC MultiRF, 2000 rpm, at 4 C, for 1 min). Lysis buffer is then added again (20 µL/well), followed by centrifugation (IEC MultiRF, 3000 rpm, at 4 C, for 5 min). The multi-well filterplate is then removed from the centrifuge and incubated (room temperature for 2 hrs).

In accordance with a preferred embodiment, the lysis buffer comprises a detergent, a salt, a pH buffer, guanidine thiocyanate, and proteinase K.

Preferred embodiments of the lysis buffer contain at least one detergent, but may contain more than one detergent. Those skilled in the art may utilize different combinations of concentrations of detergents with different strengths in order to achieve varying levels of lysis of different membranes for various types of cells. For example, IGEPAL CA-630 is a weaker detergent than N-laurosarcosine, and in one embodiment IGEPAL CA-630 alone may be sufficient to lyse a cytoplasmic membrane. In other embodiments, a strong detergent, such as N-laurosarcosine can be used in combination with one or more weak detergents to optimize lysis of nuclear membranes. The detergents are preferably sufficient to lyse at least the cytoplasmic membrane of cells. Another preferred embodiment comprises a detergent sufficient to lyse the nuclear membrane of cells, as significant amounts of mRNA reside in the nuclei of cells. In some circumstances it is desirable to measure only cytoplasmic mRNA, while in other circumstances, it may be desirable to measure mRNA in the cytoplasm and nucleus.

Strong detergents of the lysis buffer preferably include, but are not limited to: N-lauroylsarcosine, S.D.S., Sodium deoxycholate, and Hexadecyltrimethylammonium bromide.

Weak detergents include IGEPAL CA-630, N-Decanoyl-N-methylglucamine, Octyl-β-D-glucopyranoside, or other detergents known to those skilled in the art. 0.05-2% detergent can be used in the lysis buffer. One particularly preferred embodiment of the lysis buffer includes 0.5% N-lauroylsarcosine. Another preferred embodiment of the lysis buffer contains 0.1-2% IGEPAL CA-630. A particularly preferred embodiment contains 0.1% IGEPAL CA-630.

The combination of salts and chelating agents can also serve as a lysing agents. For example, 75 µM NaCl and 24 µM Na-EDTA can serve as a lysing agent. Embodiments of lysing agents may include other lysing agents known to those skilled in the art.

The salt of the lysis buffer acts as an mRNA-oligo(dT) hybridizing agent. The salt should preferably have a stringency (the rigor with which complementary DNA sequences hybridize together) that does not exceed that of 4×SSC, as determinable by those skilled in the art. Other embodiments of the lysis buffer include NaCl or other salts known to those skilled in the art.

The pH buffer of the lysis buffer stock preferably maintains a pH of 7.0-8.0. One embodiment comprises 1 mM-100 mM Tris HCl, pH 7.4. In a particularly preferred embodiment, the pH buffer comprises 10 mM Tris HCl, pH 7.4. Other preferred embodiments of the lysis buffer include pH buffers known to those skilled in the art, including 0.1 M Citrate-Phosphate, pH 5.0, with 0.03% $H_2O_2$.

Figure 11:
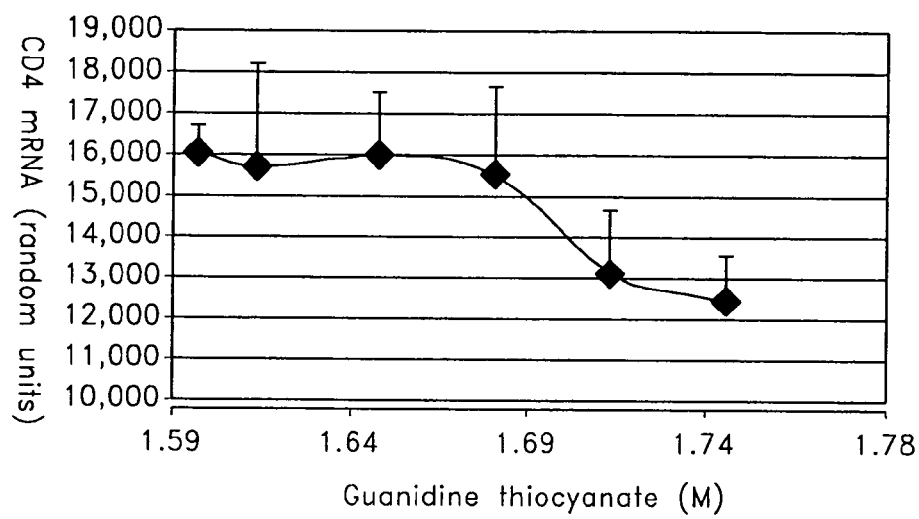
FIG. 11 is a graph showing optimal guanidine thiocyanate concentration.

In accordance with a particularly preferred embodiment of the lysis buffer, guanidine thiocyanate serves as an RNAase deactivating agent. We have discovered that guanidine thiocyanate has typically been used in the prior art at insufficient concentrations to be effective. Therefore, preferably, the concentration of guanidine thiocyanate is greater than 1.4 M. Guanidine thiocyanate concentration as high as 10 M, more preferably no higher than 2 M can be used. However, as seen in FIG. 11, at concentrations above 1.7 M, the efficiency of the lysis buffer is decreased. Accordingly, the preferred embodiment uses about 1.4 to about 1.75 M guanidine thiocyanate. One preferred embodiment comprises 1.7-1.8 M guanidine thiocyanate. A working lysis buffer can be prepared from the stock, as demonstrated in Example 4 below, with the particular concentration of 1.791 M guanidine thiocyanate. As other reagents are added to the lysis buffer, the concentration of guanidine thiocyanate becomes diluted. Where 55 ml of other reagents are added to 1 ml of the buffer as in Example 4, the preferred lysis buffer comprises guanidine thiocyanate in concentrations of about 1.61 to about 1.71 M. Thus, a preferred embodiment comprises guanidine thiocyanate in concentrations of about 1.6 to about 1.7 M.

A particularly preferred embodiment further comprises 20 mg/ml of proteinase K as an RNAase inactivating agent. One preferred embodiment of the lysis buffer comprises 200 µg/ml-20 mg/ml of proteinase K. Another preferred embodiment comprises 200 µg/ml-1.0 mg/ml proteinase K. Another preferred embodiment comprises 200 µg/ml-500 µg/ml proteinase K. Sodium dodecyl sulfate may also serve as the RNAase deactivating agent. Another embodiment includes 0.1-10% of 2-mercaptoethanol as an RNAase inactivating agent. One particularly preferred embodiment comprises 1% 2-mercaptoethanol. Other embodiments of RNAase inactivating agents may preferably include materials, known to those skilled in the art, that reduce disulfide bonds in RNAases.

Preferred embodiments of the lysis buffer further comprise chelating agents which chelate $Mg^{2+}$ and $Ca^{2+}$. One preferred embodiment comprises 0.1 mM-5 mM EDTA. A particularly preferred embodiment comprises 1 mM EDTA. Other preferred embodiments of the lysis buffer stock contain chelating agents known to those skilled in the art including, for example and without limitation, EDTMP, 2,3-dimercaptopropanol, and EGTA.

Preferred embodiments of the lysis buffer may include tRNA, which may come from various sources and is included in order to inhibit non-specific absorption of blood-derived DNA and RNA to filter plates. Additionally, the presence of tRNA prevents degradation of blood-derived RNA. In one preferred embodiment, the tRNA of the working lysis buffer comprises 10 mg/ml of E. coli tRNA. Other embodiments may contain tRNA from any source known to those skilled in the art.

Preferred embodiments of the lysis buffer may include DNA from a wide variety of sources, which is added in order to inhibit non-specific absorption of blood-derived DNA and RNA to filter plates. The DNA of the working lysis buffer preferably comprises 10 mg/ml of sonicated salmon sperm DNA. In other embodiments, DNA from other organisms may be used.

Particularly preferred embodiments of the lysis buffer may include spiked control RNA to calculate the definite quantity of target mRNAs in the original samples. Prior to embodiments of the present invention, it was difficult to compare the results in one experiment to those in other experiments due to institute-to-institute variation and lack of standardization. However, in preferred embodiments of the present invention a definite quantity of target mRNA can be determined by dividing the values obtained by the TaqMan assay with percent recovery of a dose of spiked control RNA in each sample. Such definitive quantification is described below and exemplified in Example 5.

Preferred embodiments of the lysis buffer include 10 to $1e^{10}$, more preferably $1e^{5}$ to $1e^{10}$, copies of spiked RNA per well. In preferred embodiments, the amount of control RNA used is at least enough to be detected, but not so much as to significantly interfere with the amount of target mRNA that is quantified. In preferred embodiments, the control RNA added to the lysis buffer is poly(A)$^+$ RNA. In particularly preferred embodiments where the sample being tested is human blood, the control RNA is not homologous to RNA present in human blood. In some preferred embodiments, the sequence of the control RNA is less than 90% homologous to the target mRNA, or has greater than 10% difference in length with the target mRNA. In other preferred embodiments, the sequence of the control RNA is less than 85% homologous to the target mRNA, or has greater than 5% difference in length with the target mRNA. In further embodiments, the sequence of the control RNA is less than 75% homologous to the target mRNA, or has greater than 2% difference in length with the target mRNA. In alternative embodiments, the sequence of the control RNA is less than 65% homologous to the target mRNA, or has greater than 1% difference in length with the target mRNA. In one embodiment, control RNA may preferably be made by amplifying template oligonucleotides by means of PCR. Thus, forward primers (SEQ ID NOs 10, 11, 15, and 8), reverse primers (SEQ ID NOs 9 and 16), and TaqMan probes (SEQ ID NOs 13, 17, and 12) can be used to amplify various control RNA oligonucleotides. Alternative embodiments comprise using a plurality of different target mRNAs to be quantified. Further embodiments comprise using a plurality of control RNAs.

The method involves quantification of mRNA, which in a preferred embodiment entails cDNA synthesis from mRNA and amplification of cDNA using PCR. In one preferred embodiment, the multi-well filterplate is washed with lysis buffer (150 µL/well×3 times, manual) and wash buffer (150 µL/well×3 times, manual or BioTek #G4). A cDNA synthesis buffer is then added to the multi-well filterplate (40 µL/well, manual or I&J #6). Axymat (Amgen AM-96-PCR-RD) can be placed on the multi-well filterplate, which is then placed on a heat block (37 C, VWR) and incubated (>90 min). The multi-well filterplate can then be centrifuged (2000 rpm, at 4 C for 1 min). PCR primers are added to a 384 well PCR plate, and the cDNA is transferred from the multi-well filterplate to the 384 well PCR plate. The PCR plate is centrifuged (2000 rpm, at 4 C for 1 min), and real time PCR is commenced (TaqMan/SYBER).

Figure 15:
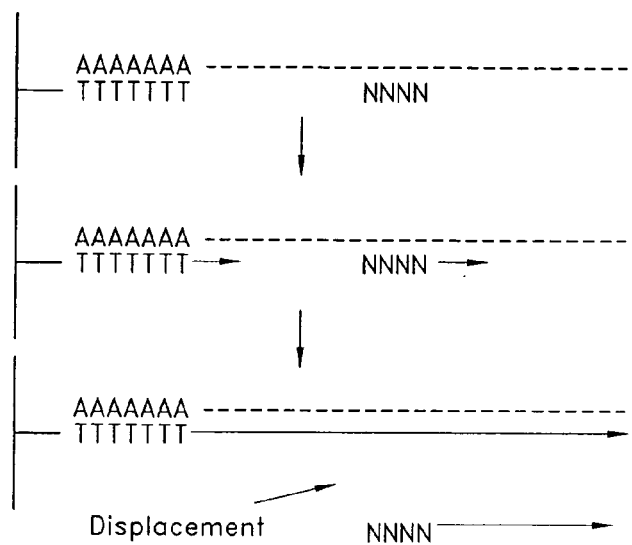
FIG. 15. shows cDNA synthesis from a specific antisense primer (NNN) and immobilized oligo(dT).
Figure 16:
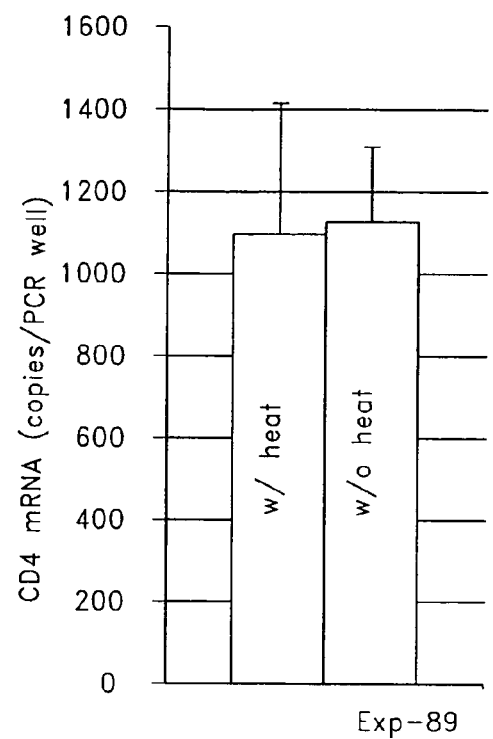
FIG. 16. is a graph showing recovery of specifically primed RNA with and without denaturization.

Another preferred embodiment comprises application of specific antisense primers during mRNA hybridization or during cDNA synthesis, as demonstrated in Example 6 below. The oligo(dT) and the specific primer (NNNN) simultaneously prime cDNA synthesis at different locations on the poly-A RNA (FIG. 15). The specific primer (NNNN) and oligo(dT) cause the formation of cDNA during amplification, as shown in FIG. 15. Even when the specific primer-derived cDNA is removed from the GenePlate by heating each well at 95 degrees C. for two minutes, the amounts of specific CD4 cDNA obtained from the heat denaturing process (using TaqMan quantitative PCR) is similar to the amount obtained from an un-heated negative control (FIG. 16). Without wishing to be bound by any explanation or theory, one possible explanation for such results is that oligo(dT)-derived cDNA may displace primer-derived cDNA during amplification (FIG. 15). This is particularly convenient because the heat denaturing process is completely eliminated. Moreover, by adding multiple antisense primers for different targets, each gene can be amplified from the aliquot of cDNA, and oligo(dT)-derived cDNA in the GenePlate can be stored for future use.

Another preferred embodiment of the invention involves a device for high-throughput quantification of mRNA from whole blood. The device includes a multi-well filterplate containing: multiple sample-delivery wells, a leukocyte-capturing filter underneath the sample-delivery wells, and an mRNA capture zone under the filter, which contains oligo (dT)-immobilized in the wells of the mRNA capture zone. In order to increase the efficiency of leukocyte collection, several filtration membranes can be layered together. The multi-well plate is fitted upon a vacuum box, which is adapted to receive the plate and to create a seal between the multi-well plate and the vacuum box. In one preferred embodiment of the device, the vacuum box is adapted to receive a source of vacuum in order to perform vacuum aspiration. In another preferred embodiment, a multi-well supporter is placed in the vacuum box, below the multi-well filterplate. In another preferred embodiment of the device, a sealing gasket, which can be made from soft plastic such as silicon-based rubber, is inserted between the multi-well supporter and the multi-well filterplate.

Although many conventional amplification techniques can be used in conjunction with the present invention, one particularly preferred embodiment of the present invention comprises conducting real-time quantitative PCR (TaqMan) with whole blood-derived RNA and control RNA. Holland, et al., PNAS 88:7276-7280 (1991) describe an assay known as a Taqman assay. The 5' to 3' exonuclease activity of Taq polymerase is employed in a polymerase chain reaction product detection system to generate a specific detectable signal concomitantly with amplification. An oligonucleotide probe, nonextendable at the 3' end, labeled at the 5' end, and designed to hybridize within the target sequence, is introduced into the polymerase chain reaction assay. Annealing of the probe to one of the polymerase chain reaction product strands during the course of amplification generates a substrate suitable for exonuclease activity. During amplification, the 5' to 3' exonuclease activity of Taq polymerase degrades the probe into smaller fragments that can be differentiated from undegraded probe. The assay is sensitive and specific and is a significant improvement over more cumbersome detection methods. A version of this assay is also described in Gelfand et al., in U.S. Pat. No. 5,210,015. U.S. Pat. No. 5,210,015 to Gelfand, et al., and Holland, et al., PNAS 88:7276-7280 (1991), which are hereby incorporated by reference.

Further, U.S. Pat. No. 5,491,063 to Fisher, et al., provides a Taqman-type assay. The method of Fisher et al. provides a reaction that results in the cleavage of single-stranded oligonucleotide probes labeled with a light-emitting label wherein the reaction is carried out in the presence of a DNA binding compound that interacts with the label to modify the light emission of the label. The method utilizes the change in light emission of the labeled probe that results from degradation of the probe. The methods are applicable in general to assays that utilize a reaction that results in cleavage of oligonucleotide probes, and in particular, to homogeneous amplification/detection assays where hybridized probe is cleaved concomitant with primer extension. A homogeneous amplification/detection assay is provided which allows the simultaneous detection of the accumulation of amplified target and the sequence-specific detection of the target sequence. U.S. Pat. No. 5,491,063 to Fisher, et al. is hereby incorporated by reference.

The TaqMan detection assays offer several advantages over the classical PCR assays. First, the TaqMan assays combine the sensitivity of PCR along with hybridization of the internal oligonucleotide sequence that is present in a target sequence. Following PCR, samples do not have to be separated on agarose gels, and the subsequent Southern blots and hybridization steps that are necessary to verify the identity of the PCR products is eliminated. These additional post-PCR confirmation steps can easily add several days for an accurate identification. Using the TaqMan system, the assays are completed within 2.5 h. Further, the methodology involved in the assay process makes possible the handling of large numbers of samples efficiently and without cross-contamination and is therefore adaptable for robotic sampling. As a result, large numbers of test samples can be processed in a very short period of time using the TaqMan assay. Another advantage of the TaqMan system is the potential for multiplexing. Since different fluorescent reporter dyes can be used to construct probes, several different HIV systems could be combined in the same PCR reaction, thereby reducing the labor costs that would be incurred if each of the tests were performed individually. The advantages of rapid, conclusive data together with labor and cost efficiency make the TaqMan detection system utilizing the specific primers of the invention a highly beneficial system for monitoring the presence of HIV.

In preferred embodiments, various mRNAs can be quantitated by simply changing primers and probes for each target. Because heparin maintains extracellular $Ca^{++}$, which is one of important factors to exert maximum biological activities, drug actions can be analyzed in whole blood without isolating leukocytes.

In preferred embodiments of the present invention, the ability to determine the total efficiency of a given sample by using known amounts of spiked standard RNA results from embodiments being dose-independent and sequence-independent. The use of known amounts of control RNA allows PCR measurements to be converted into the quantity of target mRNAs in the original samples. Such calculations can be used on large samples of individuals over time in order to determine normal ranges of presence of mRNA per µl of whole blood for various genes. When embodiments of the present invention are used to test individuals' whole blood at a given time, results indicating the presence of mRNA indicative of disease, with levels falling outside of the normal ranges, may signal the presence of disease. Embodiments of the present invention can be used as assays for the detection of various diseases. For example, mRNA indicative of a disease can be detected by inducing mRNA in many samples to a maximum desired level, measuring the mRNA of a given sample, and detecting the level of mRNA of the sample to determine if it falls below the maximum level. Similarly, embodiments of the present invention can be used as assays in determining the effectiveness of a therapeutic regimen. Embodiments of the present invention can similarly be used in oxidative stress tests, where mRNA levels of samples of people using varying amounts of anti-oxidants are compared to each other.

Another preferred embodiment involves a kit for high-throughput quantification of mRNA from whole blood. The kit includes: the device for high-throughput quantification of mRNA from whole blood; heparin-containing blood-collection tubes; a hypotonic buffer; and a lysis buffer.

Another preferred embodiment involves a fully automated system for performing high throughput quantification of mRNA in whole blood, including: robots to apply blood samples, hypotonic buffer, and lysis buffer to the device; an automated vacuum aspirator and centrifuge, and automated PCR machinery.

EXAMPLES

Example 1

Various protocols of the method of the present invention were tested and used to quantify β-actin mRNA and CD4 mRNA from whole blood.

Three anticoagulants were tested: ACD, EDTA, and heparin, with heparin resulting in the highest percent of leukocyte retention. While Leukosorb membranes have been used for ACD blood in transfusion, approximately 15-40% of leukocytes passed through even when four layers of membranes were simultaneously used. EDTA blood was tested; the capacity and leukocyte retention was found to be similar to those for ACD. Most notably, however, was that 100% of the leukocytes in heparin blood were trapped on the Leukosorb membranes. The capture of 100% of leukocytes from heparin blood shows the reliability of quantification of mRNA using the present invention. These data indicate that the use of heparin blood is most suitable for the precise quantification of mRNA, whereas ACD blood is useful for applications requiring larger volumes of blood and less quantitative results.

Figure 3:
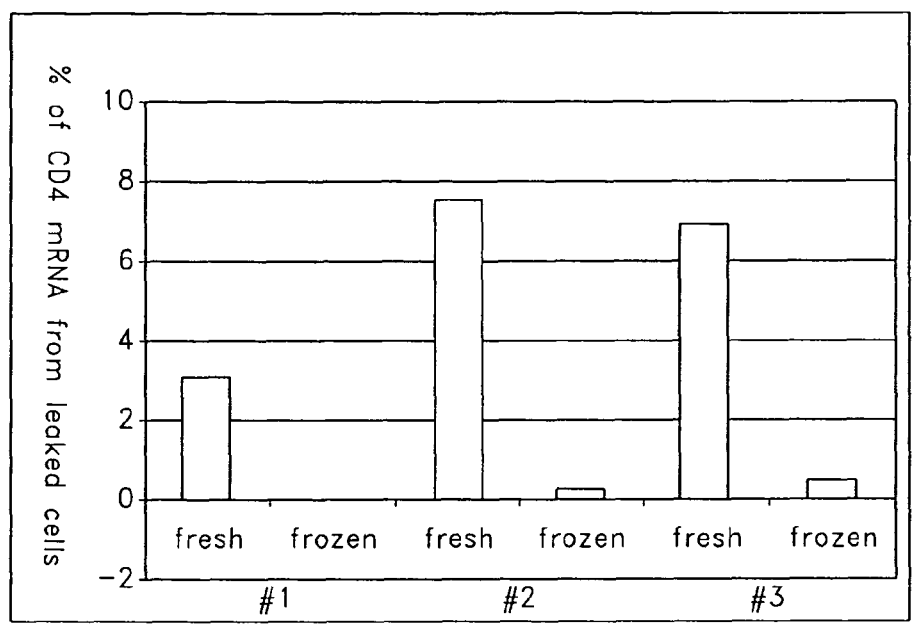
FIG. 3 is a graph showing the efficiency of leukocyte trapping of fresh and frozen blood samples on filter plates.

The results of using of frozen versus fresh blood samples were compared. As indicated in FIG. 3, more CD4 mRNA was recovered from leaked cells of fresh blood than from leaked cells of frozen samples.

The effectiveness of whole blood retention of glassfiber filters, as compared to retention values of PBT-based filter membranes, was also examined. As shown in Table II, glass-fiber membranes accepted only 40 μL of whole blood, even when membranes were washed with hypotonic buffer (50 mM Tris, pH 7.4) to burst erythrocytes. Leukosorb filters, however, accepted significantly larger amounts of whole blood than the glassfiber filters, as indicated in Table II.

TABLE II

Amplification of β-actin mRNA From Whole Blood

| Membrane | Anticoagulant*[1] | Maximum blood volume, μl/well | WBC retention (%) | Subject (n) | Tested blood volume, μl/well | ×10$^{-5}$ ng (CV$^{+5}$, %) | CT*[3] (CV*[4], %) |
|---|---|---|---|---|---|---|---|
| Glass fiber | A, E, H | 40 | 100 | #1 (9) | 20 (A)*[2] | 4.84 ± 2.80 (57.9) | 38.0 ± 0.876 (2.31) |
| | | | | #2 (9) | 20 (A) | 4.02 ± 2.52 (62.7) | 38.4 ± 0.994 (2.59) |
| Leukotrap | A, E | 3000 | 60-85 | #1 (9) | 1000 (A) | 169 ± 112 (66.0) | 33.1 ± 1.24 (3.75) |
| | | | | #2 (9) | 1000 (A) | 100 ± 72.1 (72.0) | 30.6 ± 1.42 (4.64) |
| | H | 200 | 100 | #1 (9) | 100 (H) | 18.7 ± 4.03 (21.6) | 39.2 ± 0.414 (1.01) |
| | | | | #2 (9) | 100 (H) | 15.7 ± 3.67 (23.4) | 37.8 ± 0.432 (1.06) |
| | | | | #3 (9) | 100 (H) | 15.8 ± 3.91 (24.7) | 37.7 ± 0.379 (1.01) |
| | | | | #4 (9) | 100 (H) | 15.3 ± 4.39 (28.7) | 37.7 ± 0.429 (1.14) |
| | | | | #5 (9) | 100 (H) | 13.5 ± 3.31 (24.5) | 37.9 ± 0.455 (1.20) |
| | | | | #6 (9) | 100 (H) | 20.1 ± 4.79 (23.8) | 37.3 ± 0.365 (0.98) |

Figure 4:
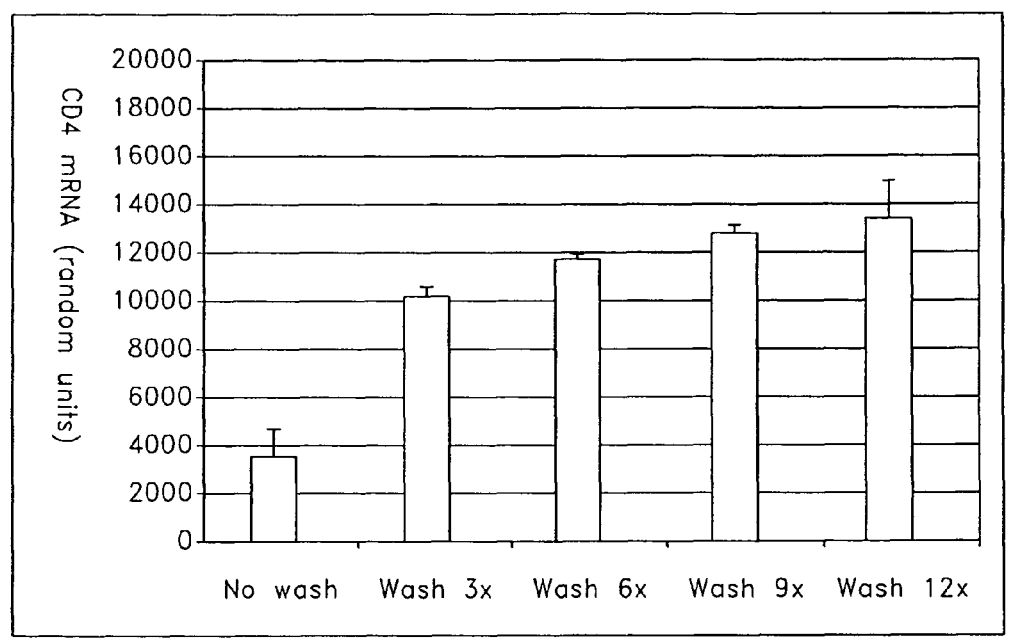
FIG. 4 is a graph showing the effect of number of washes of blood on mRNA quantification.
Figure 5:
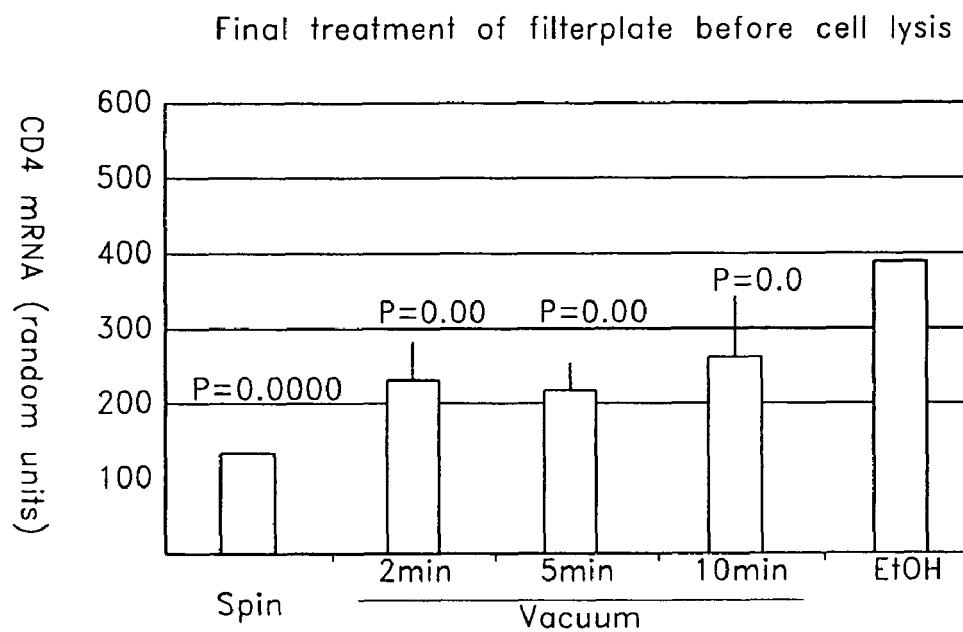
FIG. 5 is a graph showing the effect of final treatments of filter plates before cell lysis on mRNA quantification.

*[1]A: ACD, E: EDTA, H: heparin
*[2](A, H) represents anticoagulants used in the experiments.
*[3](CT: Threshold Cycle
*[4]CV: Coefficient of variation Various numbers of washes with hypotonic buffer were applied to remove erythrocytes and other blood components. As indicated in FIG. 4, washing the samples with hypotonic buffer at least three times more than doubled the amount of CD4 mRNA that was captured as compared to no washing. FIG. 4 also shows that washing the blood twelve times with hypotonic buffer resulted in the capture of the most mRNA. Additionally, various methods of vacuuming, centrifuging, and washing with ethanol followed by vacuuming blood samples to collect leukocytes were compared with respect to final CD4 mRNA quantification. FIG. 5 indicates that while vacuum aspiration resulted in better CD4 mRNA quantification than centrifugation, washing blood samples with ethanol prior to vacuum aspiration yields the most mRNA.

Figure 6:
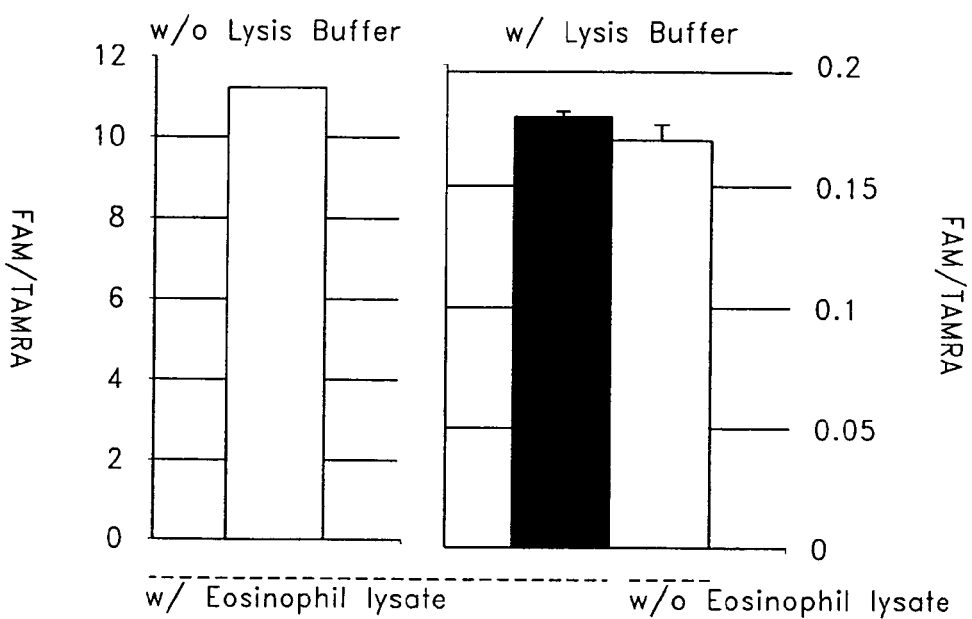
FIG. 6 is a graph showing how lysis buffer inhibits RNase.

Once the leukocytes were trapped on the glassfiber or Leukosorb membranes, various numbers of washes with hypotonic buffer were applied to remove erythrocytes and other blood components. To release mRNA from the trapped leukocytes, lysis buffer (RNAture) was applied to the filterplates (40 μL/Well), and the plates were incubated at room temperature for 20 minutes. In a preferred embodiment, amplification primers are included in the lysis buffer. FIG. 6 indicates that lysis buffer plays an important role in RNAase inhibition; eosinophils are filled with RNAases, which are inactivated by the lysis buffer. The multi-well filterplate was then sealed in a plastic bag and centrifuged (IEC MultiRF, 2000 rpm, at 4 C, for 1 min). Lysis buffer was then added again (20 μL/well), followed by centrifugation (IEC MultiRF, 3000 rpm, at 4 C, for 5 min). The multi-well filterplate was then removed from the centrifuge and incubated at room temperature for two hours to allow hybridization of poly(A)+ RNA tails with the immobilized oligo(dT). The multi-well filterplates were then washed three times with 150 μL Lysis Buffer to remove remaining ribonucleases, followed by three washes with 150 μL Wash Buffer (BioTek #G4) to remove the Lysis Buffer, which contained some inhibitors of cDNA synthesis.

Figure 7:
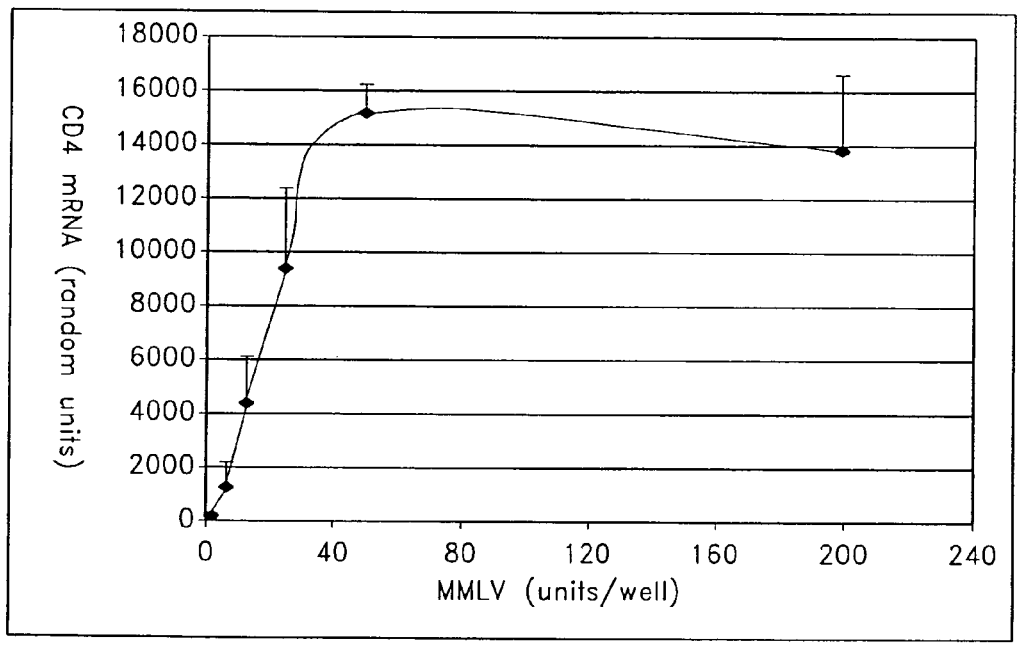
FIG. 7 is a graph showing optimal concentrations of reverse transcriptase for mRNA quantification.

Upon the final wash, the Wash Buffer was completely removed from the multi-well filterplates, and cDNA was synthesized in each well by adding 40 μL of premixed cDNA buffer. The cDNA buffer preferably consists of: 5× First Strand Buffer (Promega M531A, 10 mM dNTP (Promega stock, 20×)), Primer (5 μM, #24), RNasin (Promega N211A, 40 U/μL), M-MLV reverse transcriptase (Promega M170A, 200 U/μL), and DEPC water. FIG. 7 indicates that the optimal concentration of MMLV for mRNA quantification is 50 units/well.

Figure 8:
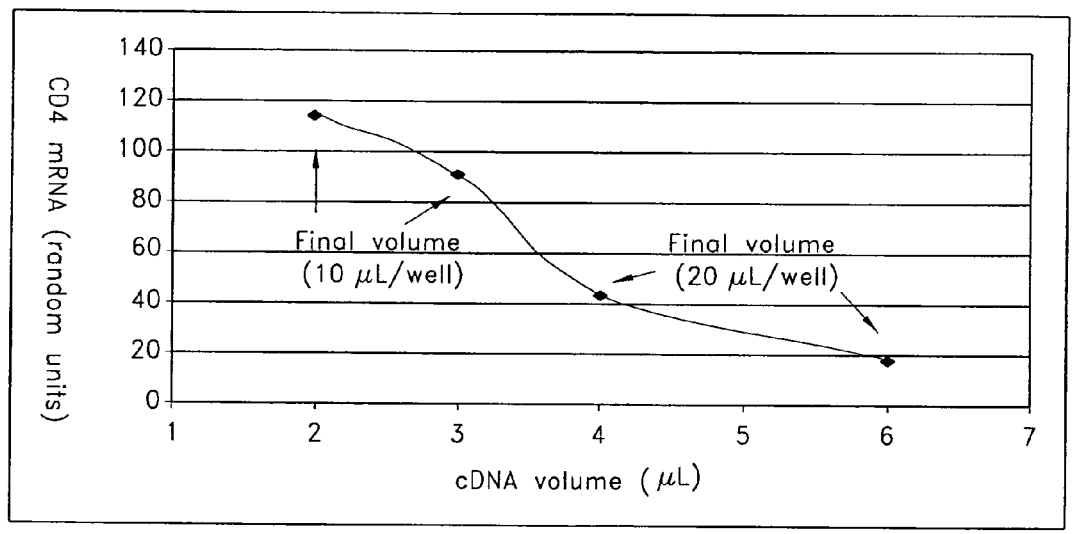
FIG. 8 is a graph showing optimal values of cDNA for PCR to capture mRNA.

Axymat (Amgen AM-96-PCR-RD) was placed on the multi-well filterplate, which was then placed on a heat block (37 C, VWR) and incubated (>90 min). The multi-well filterplate was then centrifuged (2000 rpm, at 4 C for 1 min). PCR primers were added to a 384-well PCR plate, and the cDNA was transferred from the multi-well filterplate to the 384-well PCR plate. FIG. 8 indicates that the optimal value of cDNA for PCR is approximately 2 μL/well. The PCR plate was centrifuged (2000 rpm, at 4 C for 1 min), and real time PCR was commenced (TaqMan/SYBER). The method of the current invention has high mRNA specificity; amplification of CD4 mRNA with TaqMan qPCR resulted in undetectable DNA contamination (<10 copies/well).

Figure 9:
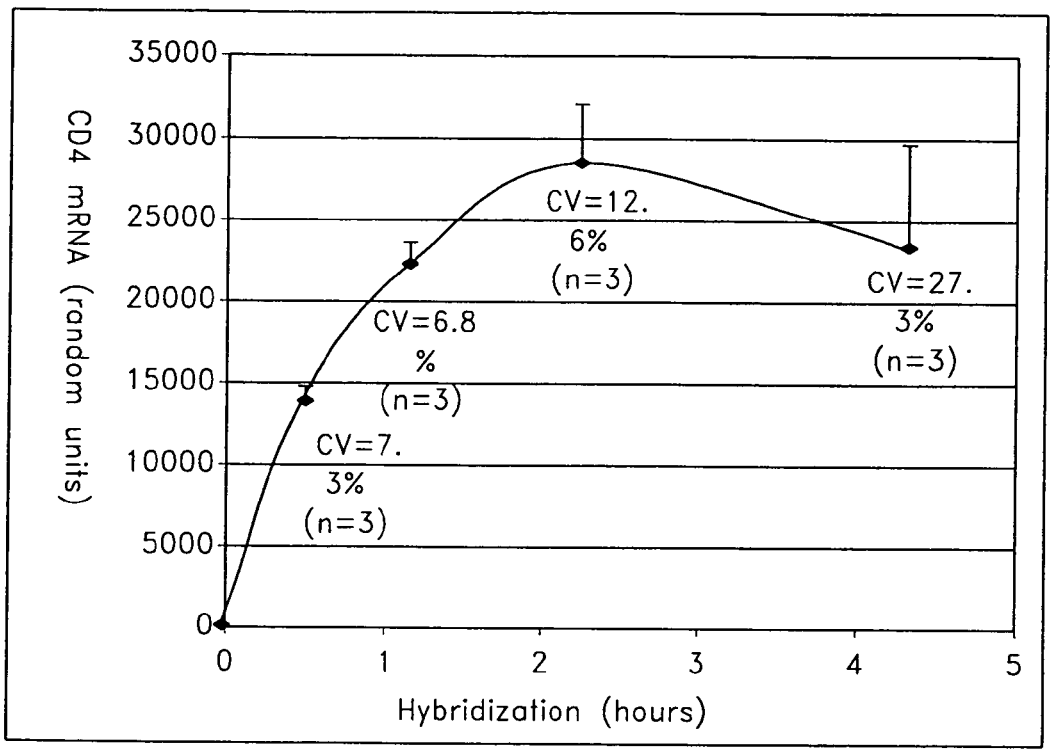
FIG. 9 is a graph showing the hybridization kinetics of the invention.
Figure 10:
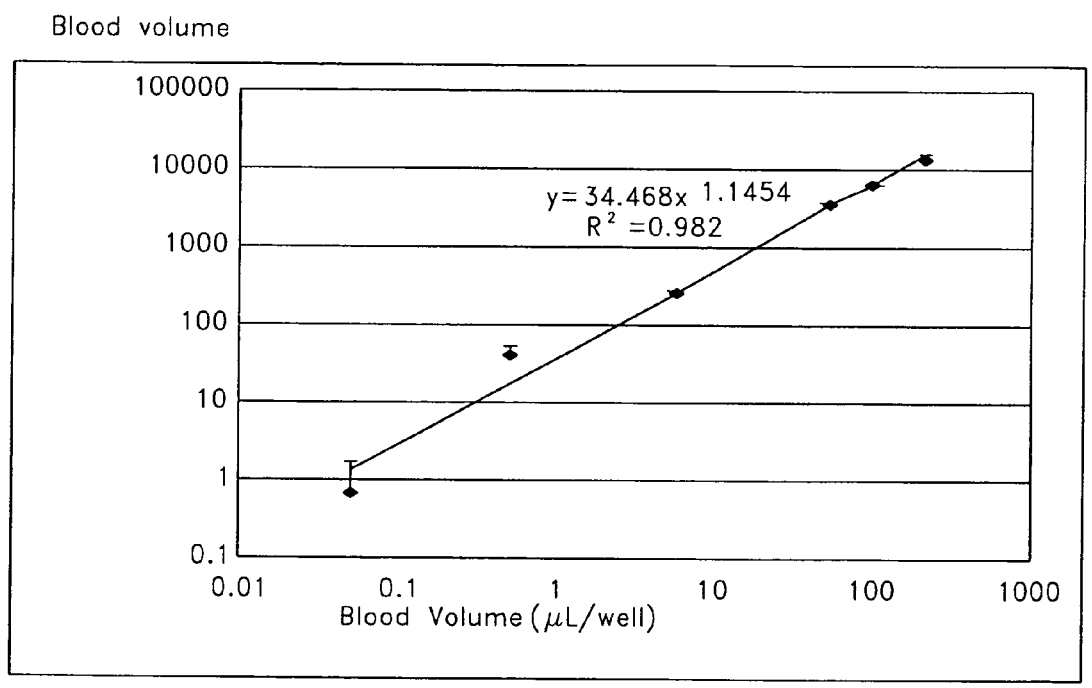
FIG. 10 is a graph showing the linear relationship between whole blood volume used per well and mRNA quantification.

As indicated in FIG. 9, the present invention results in low coefficients of variation for mRNA quantification. Hybridization for two hours resulted in a coefficient of variation of less than 13%, as compared to traditional coefficients of variation of approximately 300% for mRNA quantification. Moreover, as indicated in FIG. 10, the linear results show that the amount of mRNA that is captured is directly proportional to the volume of whole blood used per well, making the present invention a reliable and reproducible method of quantifying mRNA.

Example 2

Fifty μL of heparinized frozen human blood was applied to the Leukosorb filterplate. Each well was vacuumed and washed twelve times with 150 μL of 5 mM Tris pH 7.4 and 150 μL of 100% ethanol. Then, 40 μL of lysis buffer, which contains 1.707-1.856 M guanidine thiocyanate, was added to the well. After incubation at room temperature for 15 min, the filterplate was placed onto the GenePlate and centrifuged at 2000 rpm at 4° C. for 1 min. An additional 20 μL Lysis Buffer was added and the sample centrifuged for 5 minutes. After the GenePlate was incubated at room temperature for 2 hours, each well was washed with 100 μL Lysis Buffer 3 times, followed by three applications of 150 μL Wash Buffer (10 mM Tris, pH 7.4, 1 mM EDTA, pH 8.0, 0.5 M NaCl). The cDNA was synthesized in the GenePlate, and 2 μL cDNA was used for the TaqMan assay to quantitate CD4. The results are indicated in FIG. 11.

Example 3

Figure 12:
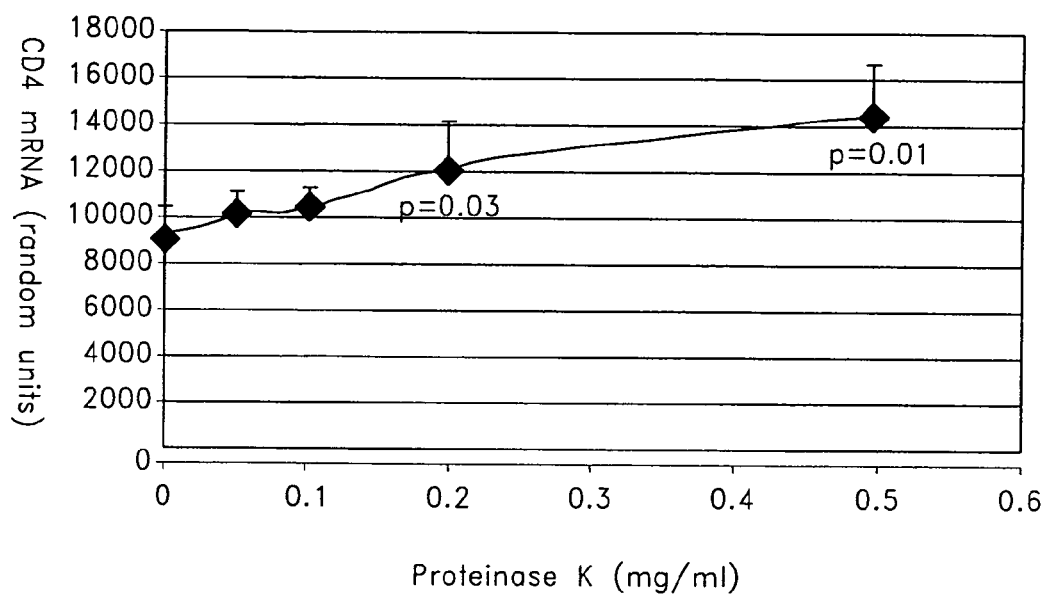
FIG. 12 is a graph showing optimal proteinase K concentration.

Fifty μL of heparinized frozen human blood was applied to the Leukosorb filterplate. Each well was vacuumed and washed twelve times 150 μL of 5 mM Tris pH 7.4, and 150 μL of 100% ethanol. Then, 40 μL of Lysis Buffer, which contains 1.791 M guanidine thiocyanate with 0-0.5 mg/ml proteinase K, was added to the wells. After incubation at room temperature for 15 min, the filterplate was placed onto the GenePlate and centrifuged with 2000 rpm at 4° C. for 1 min. An additional 20 μl, of lysis buffer was added and centrifuged again for 5 min. After the GenePlate was incubated at room temperature for 2 hours, each well was washed with 100 μL Lysis Buffer 3 times, followed by 150 μL Wash Buffer (10 mM Tris, pH 7.4, 1 mM EDTA, pH 8.0, 0.5 M NaCl) 3 times. The cDNA was synthesized in the GenePlate, and 2 μL cDNA was used for TaqMan assay to quantitate CD4. The results are indicated in FIG. 12.

Example 4

Lysis Buffer Stock 0.5% N-Lauroylsarcosine
4×SSC
10 mM Tris HCl, pH 7.4
1 mM EDTA
0.1% IGEPAL CA-630
1.791 M guanidine thiocyanate

| Working Lysis Buffer | |
|---|---|
| Lysis Buffer stock | 1 ml |
| 2-mercaptoethanol | 10 μL |
| Sonicated salmon sperm DNA (10 mg/ml) | 10 μL |
| E. coli tRNA (10 mg/ml) | 10 μL |
| Proteinase K (20 mg/ml stock) | 25 μL (final 0.5 mg/ml) |

Example 5

Preparation of control RNA. In order to synthesize control RNA, template oligonucleotides (SEQ ID NOs 2 and 4) and cDNA from K562 cells (RNAture, Irvine, Calif.) were amplified with T7-forward primers (SEQ ID NOs 3, 5, and 6) and $dT_{40}$ reverse primers (SEQ ID NOs 1 and 7) with 30 cycles of 95° C. denaturing for 30 sec, 55° C. annealing for 10 sec, followed by 72° C. extension for 20 sec, respectively. Oligonucleotides were purchased from IDT (Coralville, Iowa) or Proligo (Boulder, Colo.). The sequences were as follows:

SEQ ID NO 1: 5'-$T_{40}$-GGGTG CTGTG CTTCT GTGAA C-3',

SEQ ID NO 2: 5'-GCCCC CTCAC TCCCA AATTC CAAGG CCCAG CCCTC ACACA TTGTT CACAG AAGCA CAGCA CCC-3',

SEQ ID NO 3: 5'-GTAAT ACGAC TCACT ATAGG GGGAC AGCCC CCTCA CTCCC AAA-3',

SEQ ID NO 4: 5'-GAAGC GTGTG TCACT GTGTG TTTCC AAGGC CCAGC CCTCA CACAT TGTTC ACAGA AGCAC AGCAC CC-3',

SEQ ID NO 5: 5'-GTAAT ACGAC TCACT ATAGG GGGAC GGAAG CGTGT GTCAC TGTGT GT-3',

SEQ ID NO 6: 5'-GTAAT ACGAC TCACT ATAGG GGGAC GCATT CCGCT GACCA TCAAT A-3',

SEQ ID NO 7: $T_{40}$-TCCAA CGAGC GGCTT CAC-3'.

RNA was synthesized from purified PCR products by an in vitro transcription system (T7 RiboMax Express, Promega) at 37° C. for 30 min, followed by 15 min of DNase (1 unit) treatment twice. Purified RNA products were suspended in nuclease-free water, and the concentrations were determined by RiboGreen assay (Molecular Probes) with rRNA as a standard. The quality was analyzed by a capillary electrophoresis chip (iChip, Hitachi Chemical, Tokyo, Japan).

Leukocyte collection. Venous blood samples were collected from healthy adult volunteers. Glassfiber filterplates (RNAture) and Leukosorb membranes (Pall Life Sciences, Ann Arbor, Mich.) were obtained from the designated suppliers. Custom 96-well Leukosorb filterplates were manufactured by Whatman-Polyfiltronics (Clifton, N.J.). Since human blood samples are considered contagious materials, a disposable vacuum manifold was designed, and custom products were manufactured by Ambritt Engineering (Santa Ana, Calif.). Filterplates were placed onto the disposable vacuum manifold and washed twice with 200 μL of phosphate buffered saline (PBS: Invitrogen, carlbad, CA). The vacuum was stopped, then fresh or thawed blood samples (up to 200 μL/well) were applied to the filterplates. After all samples were dispensed into the filterplates, vacuum filtration was started with 14 cm Hg, followed by washing with PBS (200 μL/well) 12 times. After the final wash, the vacuum was continued for an additional 5 minutes to make the membranes completely dry, and the residual volume of PBS was eliminated from the membranes.

Cell lysis and mRNA preparation. Filterplates were placed onto blank microplates, followed by application of 40 μL of lysis buffer (RNAture, Irvine, Calif.), which included a reverse primer (final concentrations 25 nM), synthetic RNA as a quantitation standard, 100 μg/mL salmon sperm DNA (Eppendorf-5 Prime, Westbury, N.Y.), 100 μg/mL E. coli tRNA (Sigma), 500 μg/mL proteinase K (Pierce, Rockford, Ill.), and 1:100 dilution of 2-mercaptoethanol (BioRad, Hercules, Calif.). The sample was incubated at room temperature for 1 hour. In some experiments (FIGS. 14C-14D), various concentration of oligo $dA_{20}$ was added to the lysis buffer. Filterplates were then placed on oligo(dT)-immobilized microplates (GenePlate, RNAture), followed by centrifugation at 650×g for 1 min. 20 μL of lysis buffer was then added, followed by centrifugation at 1450×g for 5 minutes. After this process, the volume of lysis buffer in each well of the Gene-Plate was approximately 50 μL. After incubation of the Gene-Plate, the plate was washed with 100 μL plain lysis buffer 3 times, followed by washing with 150 μL wash buffer (10 mM Tris, pH 7.4, 1 mM EDTA, 0.5 M NaCl) 3 times.

cDNA synthesis. The cDNA was synthesized in a Gene-Plate by adding 30 μL of cDNA buffer, which contains 1×RT-buffer, 0.5 mM dNTP, 15 units rRNasin, and 37.5 units of MMLV reverse transcriptase (Promega). The sample was incubated at 37° C. for 2 hours. Since reverse primers were added to the lysis buffer, primers were not included in the cDNA synthesis reaction. After cDNA was synthesized, 50 μL of nuclease-free water was added into each well, and 2 μL was used for TaqMan assay, as described below.

TaqMan real time PCR. Primers and TaqMan probes for control RNA were designed by Primer Express version 2.0 (ABI, Foster City, Calif.). For bcr-abl, we used published sequences. In some experiments, HYBsimulator (RNAture) was used to design reverse primers. The forward primers (SEQ ID NOs 10, 11, 15, and 8), reverse primers (SEQ ID NOs 9 and 16), and TaqMan probes (SEQ ID NOs 13, 17, and 12) were used to amplify control RNA. In order to determine the amounts of CD4 mRNA in blood samples, both CD4 and control RNA were analyzed in the different wells of PCR plates, rather than multiplex PCR in a single well. For β-actin, commercially available primers and probes were used (ABI). Into a 384 well PCR plate (ABI) were mixed: 2 μL of cDNA, 5 μL of TaqMan universal master mix (ABI), 1 μL of 5 μM of forward primers, 1 μL of 5 μM of reverse primers, and 1 μl, of 2 μM TaqMan probe. PCR was conducted in an ABI PRISM 7900HT (ABI), using 1 cycle of 95° C. for 10 minutes, followed by 45 cycles of 95° C. for 20 seconds, followed by 55° C. for 20 seconds, and finally 60° C. for 1 minute. The data were analyzed by SDS version 2.0 (ABI). In some experiments, the TaqMan assay was conducted directly in a Gene-Plate (Opticon, MJ Research). Oligonucleotides (SEQ ID NOs 2, 4, and 14) and PCR products were used as quantitation standards for control RNA. The sequences were as follows:

SEQ ID NO 8: 5'-AAATG CCACA CGGCT CTCA-3'

SEQ ID NO 9: 5'-CAAGT GTCTT CGTGT CGTGG G-3'

SEQ ID NO 10: 5'-AGCCC CCTCA CTCCC AAA-3'

SEQ ID NO 11: 5'-AGCCC CCTCA CTCCC AAA-3'

SEQ ID NO 12: 5'-FAM-CAGTG GCTAG TGGTG GGTAC TCAAT GTGTA CTT-TAMRA-3'

SEQ ID NO 13: 5'-FAM-CCAAG GCCCA GCCCT CACAC A-TAMRA-3'

SEQ ID NO 14: 5'-CAGG GACAA ATGCC ACACG GCTCT CACCA GTGGC TAGTG GTGGG TACTC AATGT GTACT TTTGG GTTCA CAGAA GCACA GCACC CAGGG-3',

SEQ ID NO 15: 5'-CCACT GGATT TAAGC AGAGT TCAA-3'

SEQ ID NO 16: 5'-TCCAA CGAGC GGCTT CAC-3'

SEQ ID NO 17: 5'-FAM-CAGCG GCCAG TAGCA TCTGA CTTTG A-TAMRA-3'

Data analysis. The amounts of PCR products were determined using the standard curve for each gene. TaqMan results were then multiplied by the dilution factors (×40: 2 μL out of 80 μl, of cDNA was used for PCR, and ×1.67: 30 μL of cDNA was synthesized from 50 μL, of lysis buffer/well). The percent recovery of the spiked RNA was further determined for each sample by dividing recovered spiked RNA with pre-determined amounts of spiked RNA (usually $10^7$ copies per well). For CD4 mRNA, TaqMan results were multiplied by the dilution factors, divided by blood volume, and divided by percent recovery of the spiked RNA in the same sample. Each blood sample was applied to 3 wells of filterplates (triplicate), and each well produced a single cDNA and a single PCR for each gene.

Figure 13A:
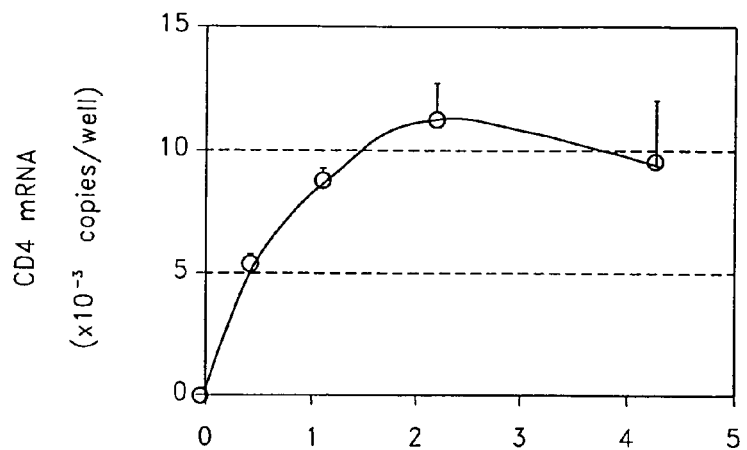
FIGS. 13A-13D are graphs showing assay validation.

Assay validation. Hybridization kinetics are shown in FIG. 13A, where hybridization reached at plateau after 2 hours at room temperature. Blood dose dependency is demonstrated in FIG. 13B, where CD4 mRNA was detected at 0.05 μL, and increased linearly up to 200 μL in log scale. We also found that the hybridization efficiency was changed dramatically between 15 and 25° C. (FIG. 13C). As shown in FIG. 13D, CD4 mRNA was very stable in heparinized blood and almost unchanged up to 7 hours at 37° C. or overnight at 4° C. This suggests that CD4 may be a good control for gene expression analysis in whole blood. The results in FIG. 13 were expressed as the mean±standard deviation of the number of genes. Although the CV of cycle threshold (Ct) was less than 1-2%, it increased substantially when Ct was converted to the number of genes via the transformation from log to linear scales. However, as shown in FIG. 13, the CV was as low as 10-30% even when the starting materials were whole blood.

Figure 14A:
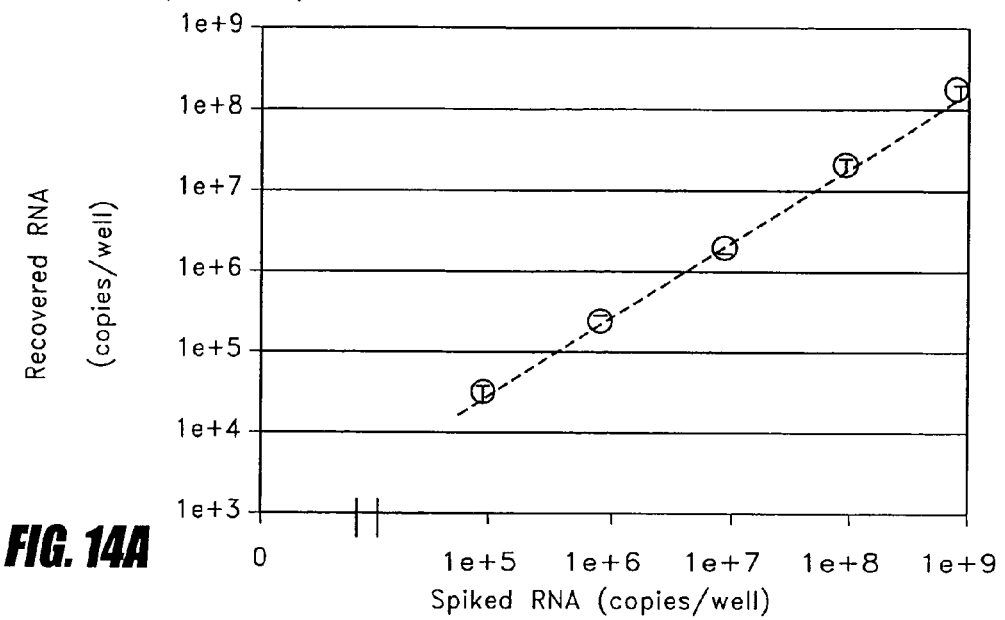
FIGS. 14A-14D are graphs showing recovery of synthetic spiked RNA.
Figure 14B:
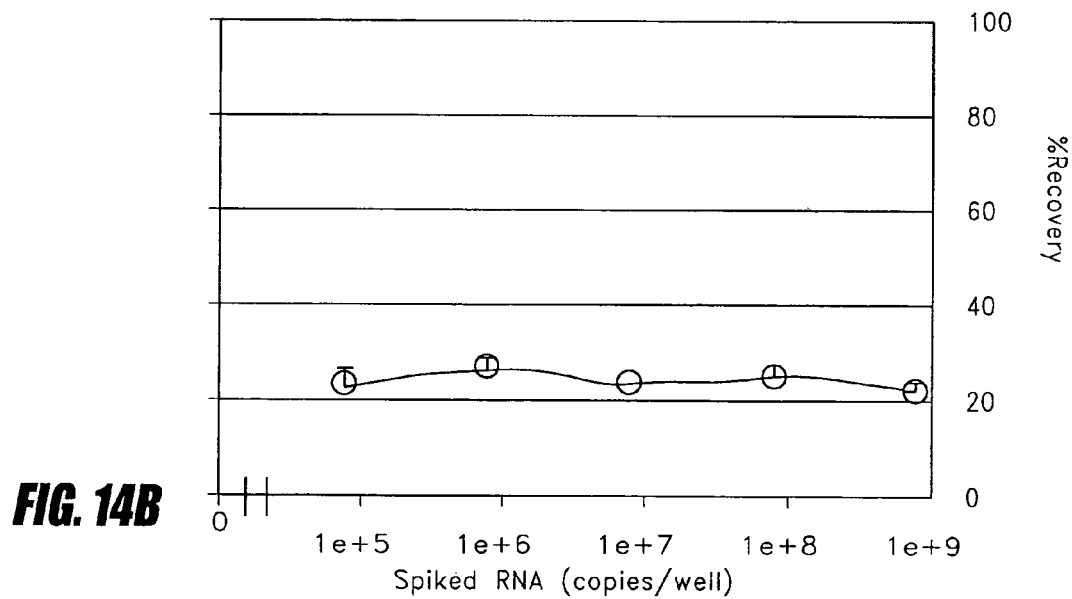

Quantitation. The goal of quantitation in this study was to determine the total assay efficiency in each sample by using spiked control RNA, which is further used as a denominator to calculate the definite quantity of target mRNAs in the original samples. The principle includes two assumptions: that the recovery of RNA is dose-independent, and that recovery is species-independent. In other words, percent recovery should be identical between high and low copy number mRNAs, and also identical among different sequences. These assumptions are not only applied to the step of mRNA purification, but also to whole processes of mRNA quantitation, from cell lysis to PCR. In order to validate the first assumption, different amounts of synthetic poly(A)$^+$ control RNA were added into the lysis buffer and exposed to Leukosorb membranes, where 50 μL of blood was applied. After we confirmed that the control RNA was not amplified from human blood alone, the recovery of the control RNA was determined by a TaqMan assay. As shown in FIG. 14A, dose-dependent recovery of control RNA was observed at the tested range of $10^5$ to $10^9$ copies/well. When the same data were converted to percent recovery, these values became similar around 20% (FIG. 14B). The data of FIGS. 14A and 14B were the sum of whole processes, which include mRNA purification and cDNA synthesis. Under the equilibrium condition of hybridization, the dissociation constant (Kd) was calculated as follows:

Kd=[RNA]×[oligo-dT]/[RNA:oligo-dT]; where [RNA] and [oligo-dT] represent the concentrations of unbound states of RNA and oligo-dT, respectively, and [RNA:oligo-dT] represents the concentrations of hybridized RNA with oligo-dT. This means that [RNA:oligo-dT] is variable of the amounts of applied RNA. In fact, [RNA:oligo-dT] was increased in proportion to the amounts of applied RNA, when hybridized RNA was measured by Yoyo-1 nucleic acid dye (Miura, Y., Ichikawa, Y., Ishikawa, T., Ogura, M., de Fries, R., Shimada, H., & Mitsuhashi, M. Fluorometric determination of total mRNA with oligo(dT) immobilized on microtiter plates. *Clin Chem.* 42, 1758-64 (1996)). However, because the control RNA in FIG. 14B is a very small fraction of the total mRNA in each well, it does not practically influence the values of Kd at this range. When primers were included in the step of cDNA synthesis, we faced a problem of intra- and interspecies reproducibility. However, by adding primers during hybridization, reproducibility improved, suggesting that cDNA is equally synthesized from pre-hybridized primers, even when primer sequences are different. Although percent recovery itself may vary among individuals dependent on the amounts of mRNA in samples, FIGS. 14A and 14B indicate that percent recovery derived from one concentration can apply to other concentrations within the same samples.

Figure 14C:
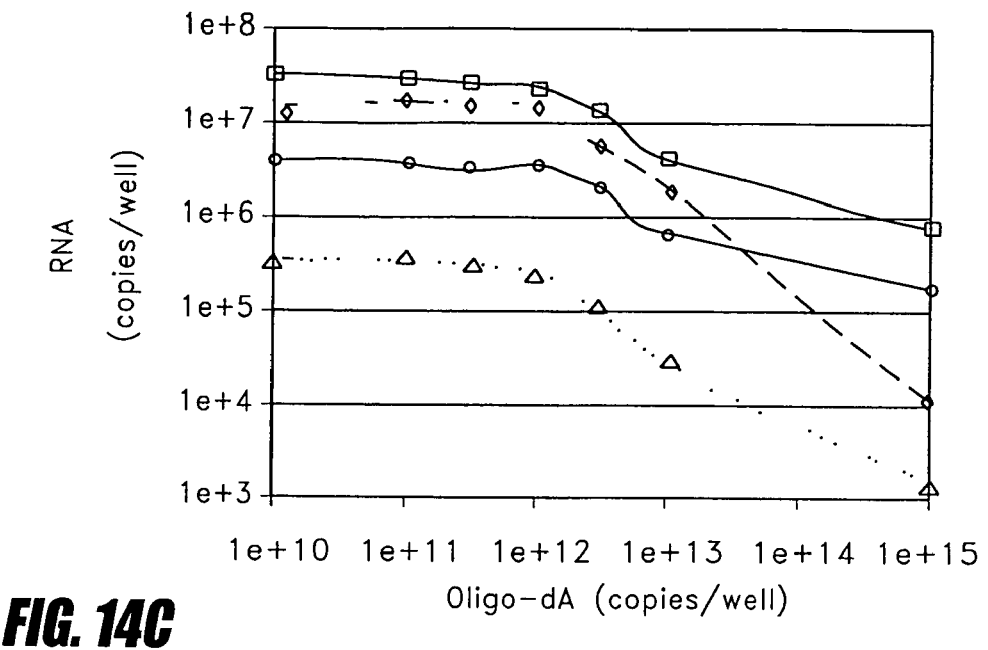
Figure 14D:
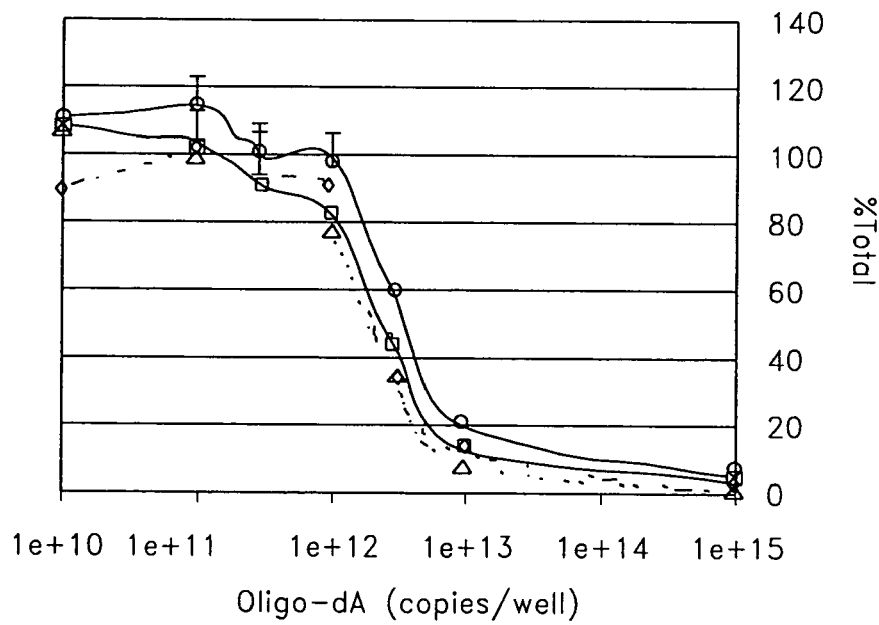

To test the second assumption, that recovery is species-independent, hybridization was competitively inhibited by oligo-dA in lysis buffer, where three synthetic poly(A)$^+$ RNAs were included. As shown in FIG. 14B, the amounts of recovered RNA varied among three spiked RNAs as well as target native CD4 mRNA, because we intentionally used different amounts of RNAs. However, all RNAs were inhibited by oligo-dA at $3 \times 10^{12}$-$10^{15}$ copies/well (FIG. 14C). Interestingly, when the same data were transformed to the percent total, all four RNAs showed very similar inhibition curves with an $IC_{50}$ of around $3 \times 10^{12}$ copies/well (FIG. 14D). This suggests that mRNA purification in our system is poly(A)-specific and sequence-independent. As shown in FIG. 14C, some non-specific activity remains even after $10^{15}$ copies of oligo-dA were applied. However, as shown in FIG. 14D, this non-specific activity was less than 5% of total activity. Thus, non-poly(A) sequences do not appear to play a major role in this assay. Because FIGS. 14B and 14C were the sum of whole processes of mRNA quantitation, these graphs suggest that the assay efficiency of target genes is identical to that of spiked synthetic RNA, even when sequences are different. This also indicates that the definite quantity of target mRNA can be determined by dividing the values obtained by TaqMan assay with percent recovery of single dose of spiked control RNA in each sample.

Intra-assay variation was approximately 10-20%, as shown in FIGS. 13 and 14. In order to assess inter-assay variation, seven different experiments were conducted by using the same frozen blood aliquots, in addition to fresh or frozen blood from the same individual. In each experiment, different filterplates and GenePlates were used, and fresh materials were prepared for lysis, cDNA synthesis, and PCR. As shown in Table III below, percent recovery of control RNA was 4-29%. When we compared the amounts of CD4 without considering control RNA recovery, these values varied widely. However, after adjusted with percent recovery in each sample, the values became very similar with an inter-assay CV of 7-14%.

Figure 13B:
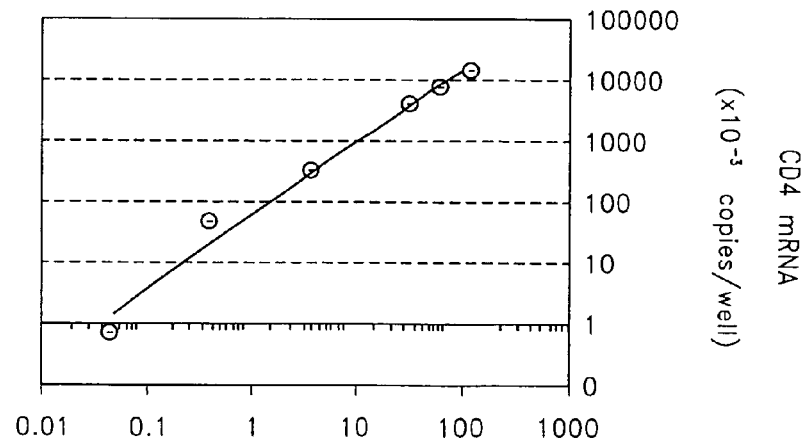
Figure 13C:
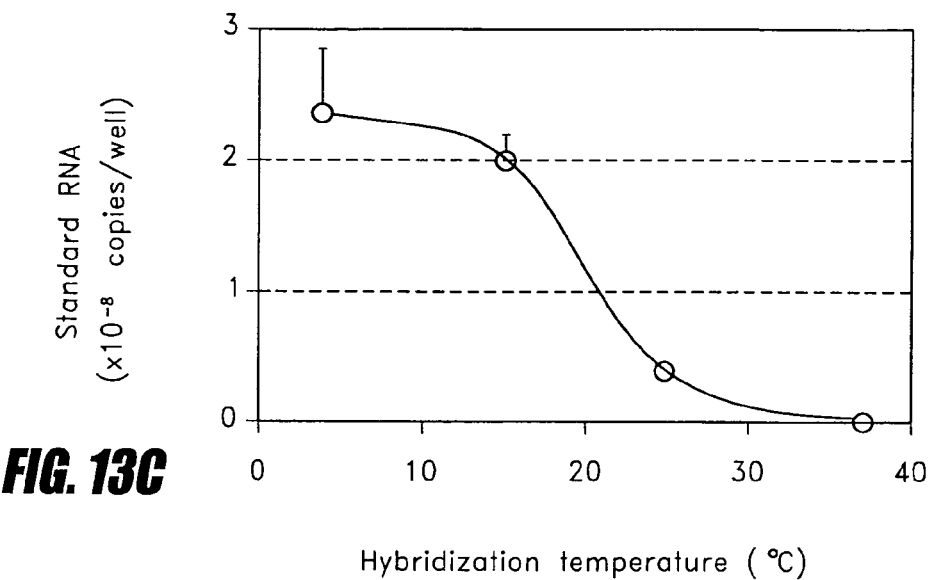
Figure 13D:
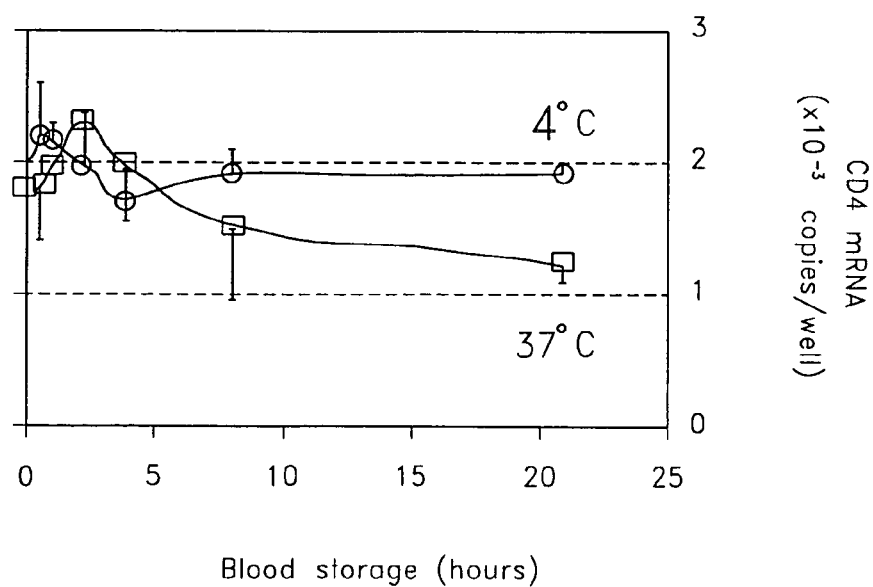

FIGS. 13A-13D demonstrate assay validation. TaqMan assays were conducted from cDNA derived from 50 μL of heparinized human whole blood (FIGS. 13A, B, D) or synthetic control RNA (FIG. 13C). FIG. 13A shows hybridization kinetics. Blood aliquots were frozen at −80° C. Identical blood aliquots were thawed at different times, and applied to filterplates to adjust the hybridization length from 30 to 270 minutes at room temperature. FIG. 13B shows dose responses. Blood was diluted with PBS 10, 100, and 1000 folds, and 50-200 μL samples were applied to filterplates. FIG. 13C shows hybridization temperature. Hybridization was conducted at 4, 15, 25, and 37° C. for 2 hours. FIG. 13D shows the stability of heparinized whole blood. After blood samples were stored at 4 or 37° C. for various lengths of time, each sample was individually frozen. Samples were thawed simultaneously and applied to filterplates. The data were expressed as the mean±standard deviation.

FIGS. 14A-14D represent recovery of synthetic spiked RNA. In FIGS. 14A and 14B, 0-$10^{10}$ copies of RNA34 were applied to each well. After conducting mRNA purification and cDNA synthesis, the amounts of control RNA were determined by TaqMan PCR. FIG. 14A shows the amounts (copy number) of recovered control RNA versus the amounts of added control RNA. FIG. 14B shows percent recovery, which was calculated as follows:

% Recovery=Amounts of recovered control RNA/
amounts of added control RNA×100.

FIGS. 14C and 14D show percent recovery in the presence of Oligo-dA. After 50 μL of heparinized blood was applied to Leukosorb filterplates, lysis buffer containing various amounts of control RNA34 (□), control RNA36 (○), and control bcr-abl (Δ) were applied to each well along with 0-$10^{15}$ copies of oligo-dA$_{20}$. After mRNA purification and cDNA synthesis, the amounts of control RNA were determined by TaqMan PCR. FIG. 14C shows the amounts (copy number) of recovered RNAs versus the amounts of oligo-dA$_{20}$. In FIG. 14D the percent total was calculated as follows:

% Total=Amounts of recovered RNA with oligo-$dA_{20}$/
amounts of recovered RNAs without oligo-$dA_{20}$×
100.

Example 6

Fifty μL of heparinized human blood were applied to a filterplate, where four layers of Leukosorb membranes were

TABLE II

Summary of spiked RNA recovery and CD4 mRNA quantitation

| | | Spiked RNA | | | CD4 | | | |
| | | standard curve | | | standard curve | | | copies/μL |
| Subject | Fresh/Frozen | A* | B* | % Recovery | A* | B* | copies/μL | (adjusted) |
| --- | --- | --- | --- | --- | --- | --- | --- | --- |
| #1 | Frozen | −0.18 | 10.06 | 12.29 ± 10.34 | −0.24 | 13.00 | 805,901 ± 163,607 | 6,534,803 ± 1,168,123 |
| #1 | Frozen | −0.19 | 10.21 | 4.70 ± 0.37 | −0.23 | 12.95 | 358,894 ± 56,669 | 7,613,541 ± 657,139 |
| #1 | Frozen | −0.20 | 10.47 | 11.79 ± 1.31 | −0.20 | 12.40 | 822,329 ± 422,666 | 7,240,998 ± 4,486,279 |
| #2 | Fresh | −0.17 | 9.82 | 29.13 ± 1.17 | −0.17 | 11.15 | 1,731,727 ± 90,901 | 5,943,401 ± 170,939 |
| #2 | Fresh** | −0.20 | 10.47 | 4.26 ± 0.88 | −0.20 | 12.40 | 357,278 ± 252,136 | 5,524,693 ± 3,434,592 |
| #2 | Frozen | −0.20 | 10.47 | 12.27 ± 1.62 | −0.20 | 12.40 | 557,028 ± 220,087 | 4,477,879 ± 1,384,554 |

*: Copy number = $10^{\wedge}(A \times Ct + B)$.
**: Second blood was drawn from the same individual 2 days after the first one.

attached. The blood was vacuum aspirated and washed with 150 μL of 5 mM Tris (pH 7.4) twelve times. The filterplate was then placed on a GenePlate, and 40 μL of lysis buffer (with or without antisense primer for CD4) were applied to each well. Cell lysates were transferred from the filterplate to the GenePlate by centrifugation. This process was repeated once with 40 μL of lysis buffer. After the GenePlate was incubated at room temperature for 2 hours, each well was washed with 100 μL of Lysis Buffer three times, followed by three applications of 150 μL wash buffer. The cDNA was synthesized in each well of the GenePlate by adding cDNA synthesis buffer and appropriate enzymes. After 37° C. incubation for two hours, each well was washed three times with 150 μL of 95° C. water. Then, CD4 mRNA was detected in the GenePlate by TaqMan real time PCR.

Figure 17:
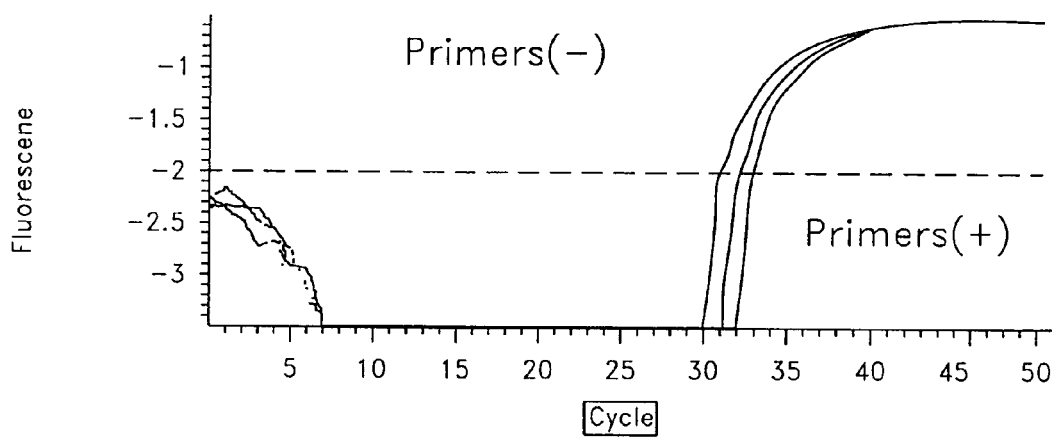
FIG. 17. is a graph showing amplification of RNA with and without specific primers.

In order to validate the hypothesis that oligo(dT) displaces specifically-primed (by NNNN) cDNA, cDNA was synthesized in the GenePlate with or without specific primers. Then, the CD4 gene was amplified directly from the GenePlate. As shown in FIG. 17, CD4 was amplified from both samples. This suggests that upstream cDNA is displaced from immobilized oligo(dT)-derived cDNA.

Example 7

Figure 18A:
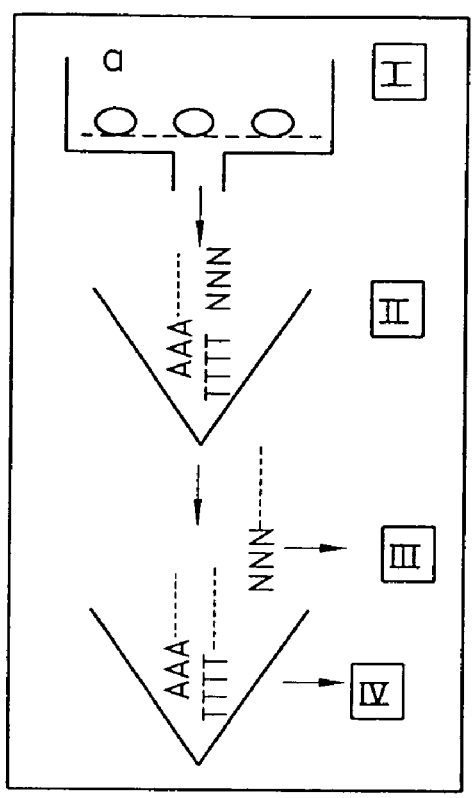
FIG. 18A shows a typical mRNA capture scheme of the present invention.
Figure 18B:
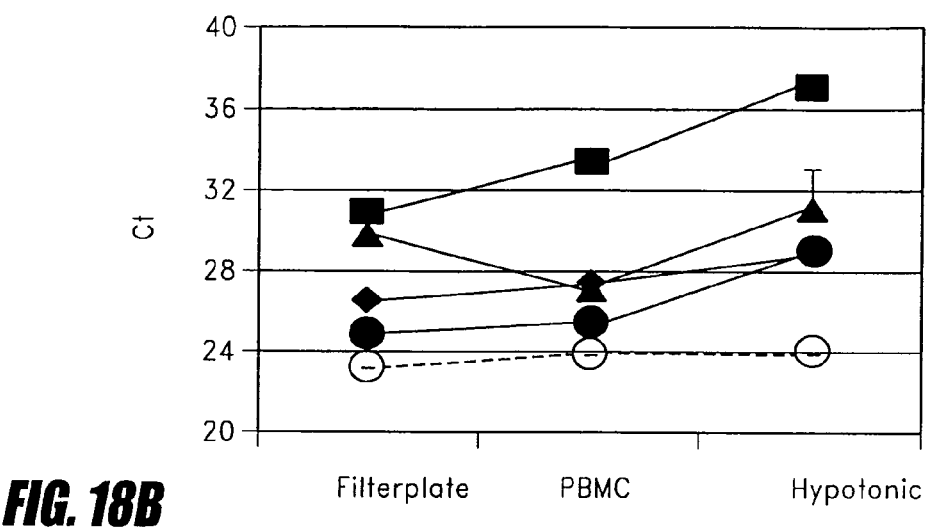
FIG. 18B is a graph showing various hybridization performances.

Overall Scheme. As illustrated in FIG. 18A, whole blood is applied to filterplates to trap leukocytes (I). After washing the filterplates with phosphate buffered saline (PBS, Invitrogen), erythrocytes and plasma components are removed. This process is simpler and higher throughput than that of conventional density gradient separation of peripheral blood mononuclear cells (PBMC). As shown in FIG. 18B, (standard RNA (○), CD4 (●), p21 (▲), FasL (◆), and leukotrien C4 synthese mRNA (LTC4S) (■)) the filterplate's hybridization performance was slightly better than that of the density gradient method. The levels of leukotrien C4 synthese (LTC4S) mRNA was significantly less in PBMC, possibly due to the elimination of the granulocyte population. However, p21 mRNA was significantly higher in PBMC, due to secondary induction during the lengthy separation processes (FIG. 22). Another method was compared, wherein whole blood was centrifuged and the pellets were suspended in hypotonic solution (10 mM KHCO$_3$, 15 mM NH$_4$Cl, 0.14 mM EDTA, pH 7.2) to burst the erythrocytes, followed by immediate centrifugation to precipitate the leukocytes (FIG. 18B: Hypotonic). However, the levels of CD4, p21, FasL, and LTC4S were all less than those of the filterplate method.

Figure 18C:
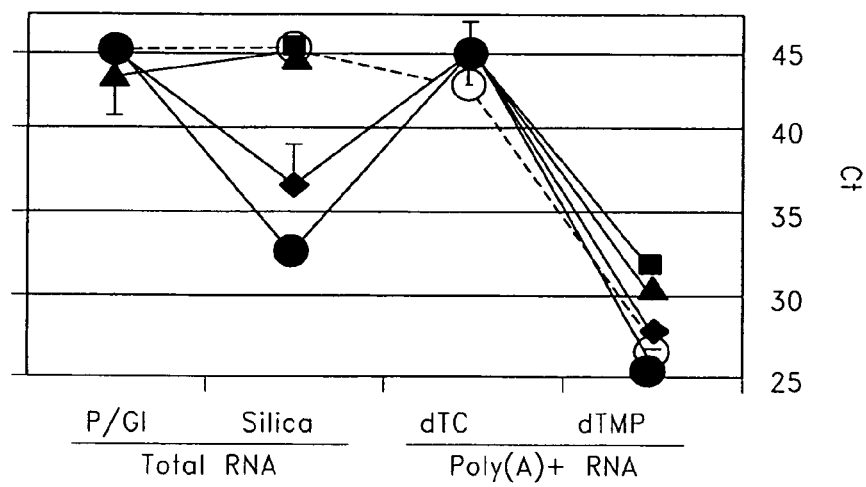
FIG. 18C is a graph showing efficiency of various methods of capturing total RNA and Poly(A) RNA.

As shown in FIG. 18A (II), the next step was to apply lysis buffer to the filterplates and to transfer the lysate to oligo(dT)-immobilized microplates for mRNA purification. In order to evaluate this process, three other methods were employed for comparison. Phenol/guanidine isocyanate (Trizol, Invitrogen) (FIG. 18C: P/GI) or kit-supplied Lysis Buffer (RNeasy, Qiagen) (FIG. 18C: Silica) was applied to each well of the filterplates, followed by the precipitation of RNA (P/GI) or elution of RNA from a spin column (Silica) according to the instruction manuals of the products. For direct purification of poly(A)+ RNA, lysis buffer was applied to the filterplates, and lysates were transferred to either oligo(dT)-immobilized microplates (GenePlate, RNAture) (FIG. 18C: dT MP) or fresh microtubes, which contain oligo(dT) cellulose (Invitrogen) (FIG. 18C: dT C). While P/GI, Silica, and dT C methods exhibited sufficient performance when large amounts of isolated PBMC was used in microtubes, these methods did not work well with the filterplate system, where only 50 μl blood was used (FIG. 18C). Moreover, when cell pellets are lysed in tubes, the degree of mechanical strength (vortex or pipetting) is critical to release mRNA, and this process creates substantial variation. However, with the filterplate method cells were dispersed within the membrane, and application of lysis buffer was sufficient enough to work without the need for any added mechanical force.

Figure 18D:
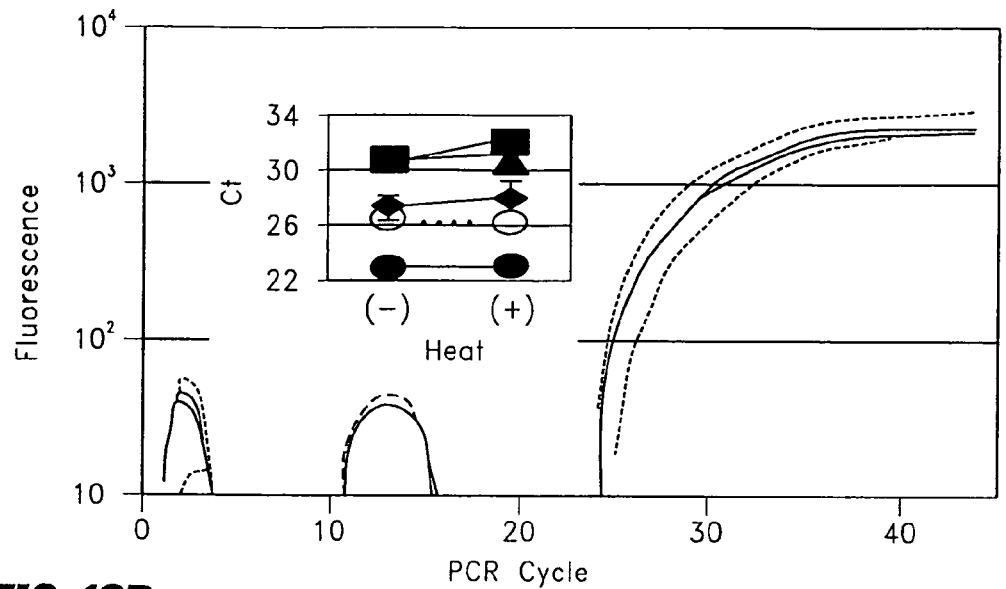
FIG. 18D is a graph showing the optimal number of PCR cycles.

Since the lysis buffer preferably contains a mixture of primers, two independent hybridization reactions took place simultaneously (FIG. 18A). One occurred between immobilized the immobilized oligo(dT) and the poly(A) tails of mRNA. The other hybridization reaction took place between specific primers and appropriate sites in mRNA (FIG. 18A (II)). Although the design of specific primers is critical, sufficient hybridization time made the assay more reproducible than that of primer hybridization during cDNA synthesis. It first appeared as though cDNA-mRNA duplex stayed in the solid surface via hybridization with immobilized oligo(dT) (FIG. 18A (II)). Thus, cDNA was removed from the solid surface by heating at 95° C. for 5 min. However, the amounts of amplified genes were unchanged to those of un-heated control (FIG. 18D inset). To test whether the cDNA-mRNA duplex was somehow removed from the solid surface, microplates were washed with water extensively after cDNA synthesis, and used for PCR directly. However, the target gene was successfully amplified from microplates with or without specific primers during the hybridization step (FIG. 18D). These data suggest that the specific primer-primed cDNA may be displaced with oligo(dT)-primed cDNA (FIGS. 18A (III, IV)). This makes the system advantageous; because the cDNA in solution is used for gene quantitation, the microplate itself can be used as a cDNA bank for validation, storage, and future use.

Figure 18E:
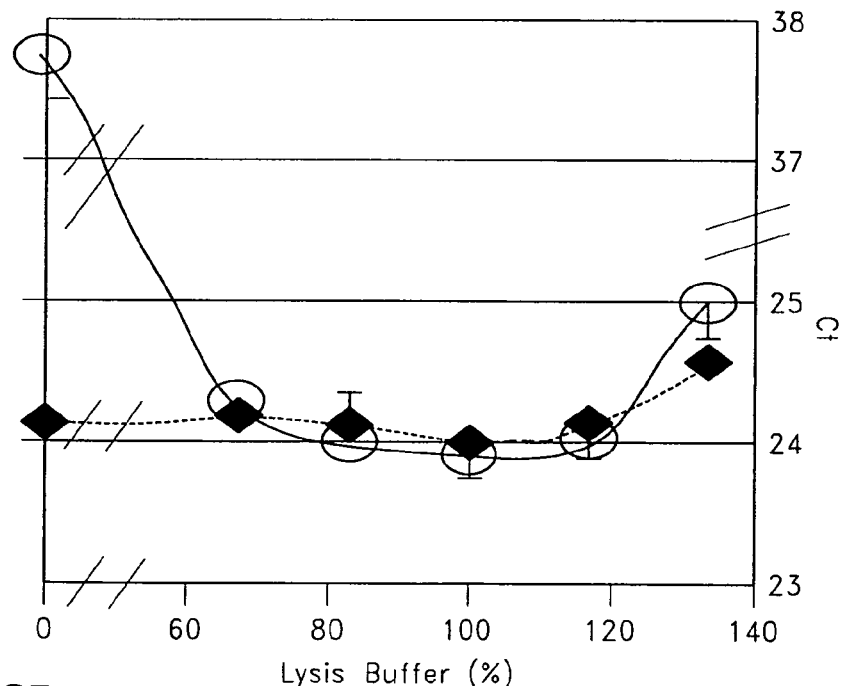
FIG. 18E is a graph showing the optimal range of lysis buffer for capture of RNA.

In order to validate RNA stability during lysis and subsequent hybridization processes, various concentrations of lysis buffer containing equal amounts of standard RNA were diluted with water or concentrated eosinophil extract. As shown in FIG. 18E, the eosinophil extract itself largely abolished standard RNA quantitation when it was suspended with wash buffer (10 mM Tris, pH 7.4, 1 mM EDTA, 0.5 M NaCl), where hybridization stringency was maintained without major lysis buffer components. However, when eosinophil extract was suspended in the lysis buffer, RNA was maintained, and was similar to that of water dilution (FIG. 18E). The wide range of optimal lysis buffer concentrations (70-120%) made this system robust and reproducible. Lysis buffer concentrations higher than 140% significantly reduced the assay performance.

Figure 19A:
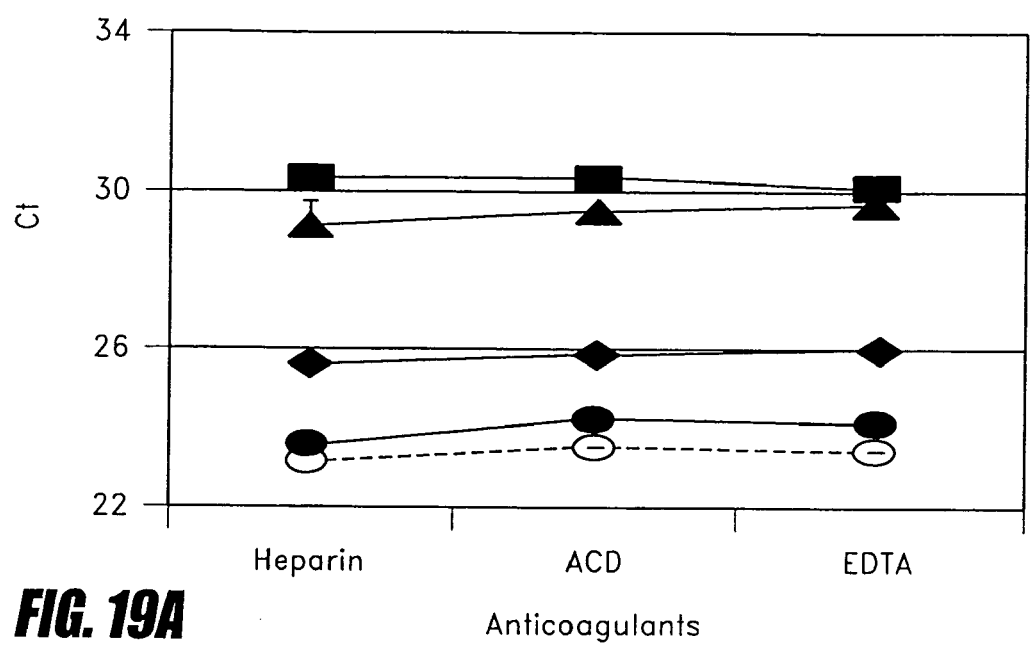
FIG. 19A is a graph showing number of PCR cycles versus various anticoagulants.

Assay optimization. Studies were conducted to identify the optimal, reproducible conditions that exhibit equal performance among five different target RNAs, as illustrated in FIGS. 19A-F (standard RNA (○), CD4 (●), p21 (▲), FasL (◆), and leukotrien C4 synthese mRNA (LTC4S) (■)). The reproducible conditions are critical for the subsequent gene quantitation section. Each data point in FIG. 19 is the mean±standard deviation (s.d.) from triplicate blood aliquots (50 μl each) from a single typical experiment. However each experiment was reproduced at least two to three times. First, three typical anticoagulants were tested. Although heparin exhibited slightly better performance than ACD and EDTA, all 3 anticoagulants are acceptable (FIG. 19A). Since ACD and EDTA chelate calcium, which is a critical component for many biological activities, heparin was the choice of anticoagulant of this project where whole blood will be used for stimulation in vitro (FIG. 22).

Figure 19B:
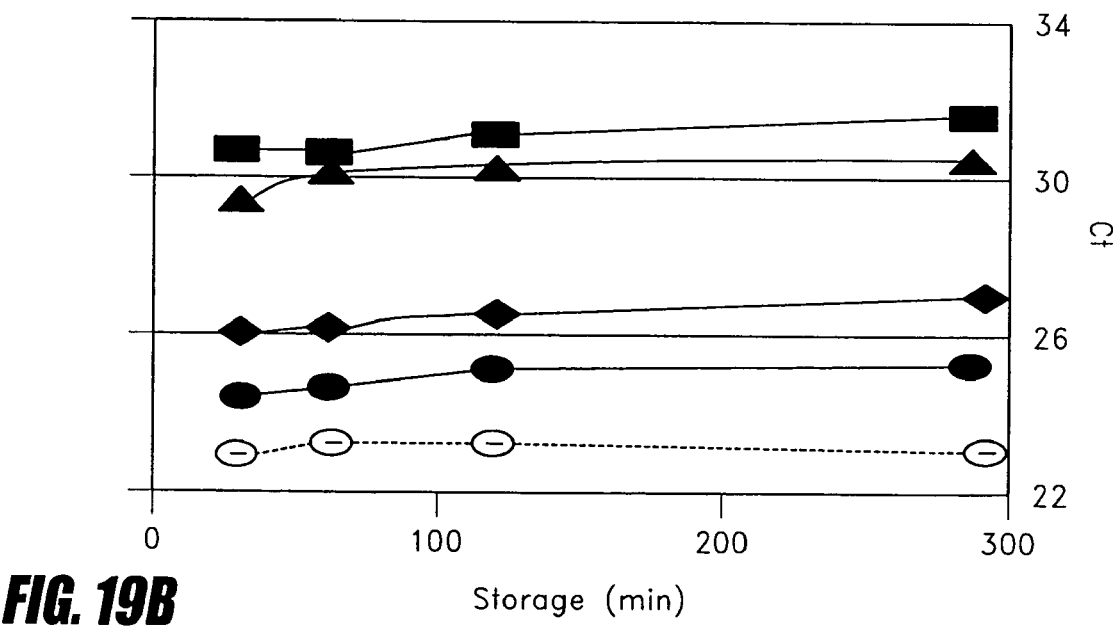
FIG. 19B is a graph showing number of PCR cycles versus storage time.

Maintaining the stability of whole blood after drawing blood is a prime concern. Thus, some commercial systems (PAX gene, PreAnalytix) uses special blood container, where cells are lysed immediately, and released RNA is stabilized for a relatively long period. However, manipulation of large volumes of lysate make entire systems problematic. Moreover, because one of the goals of this project is to quantitate mRNA before and after gene induction processes in vitro (FIGS. 22A-H), heparinized whole blood was stored at 4° C. and the changes in mRNA levels were examined. Although the levels of four native genes (CD4, p21, FasL, and LTC4S) were not stable after the blood draw, the levels became stable and constant after two hours whenever blood was stored at 4° C. (FIG. 19B).

Figure 19C:
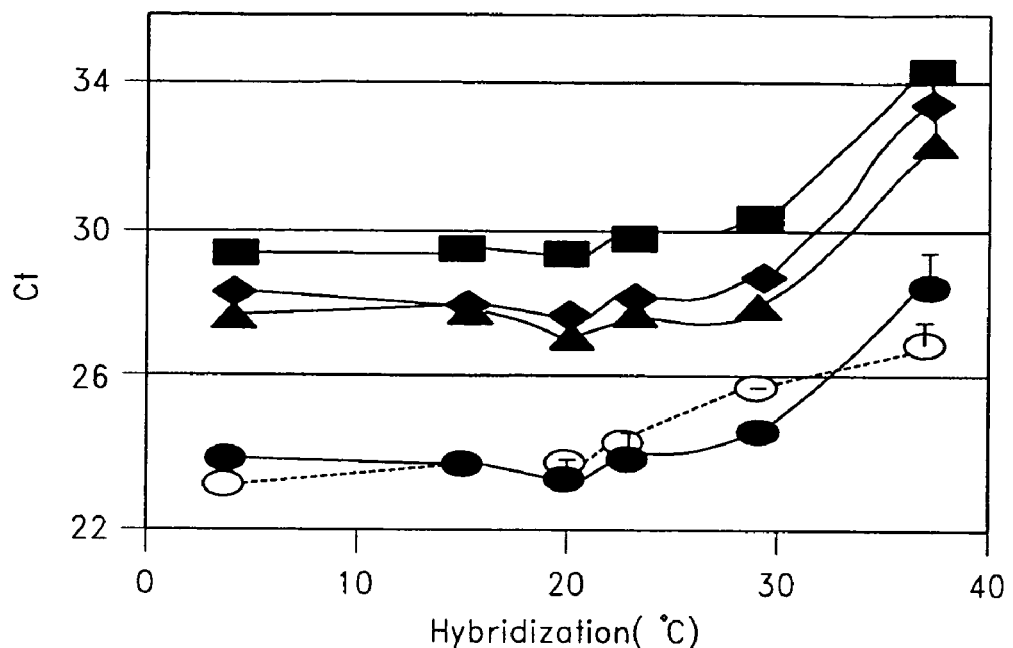
FIG. 19C is a graph showing number of PCR cycles versus hybridization temperature.
Figure 19D:
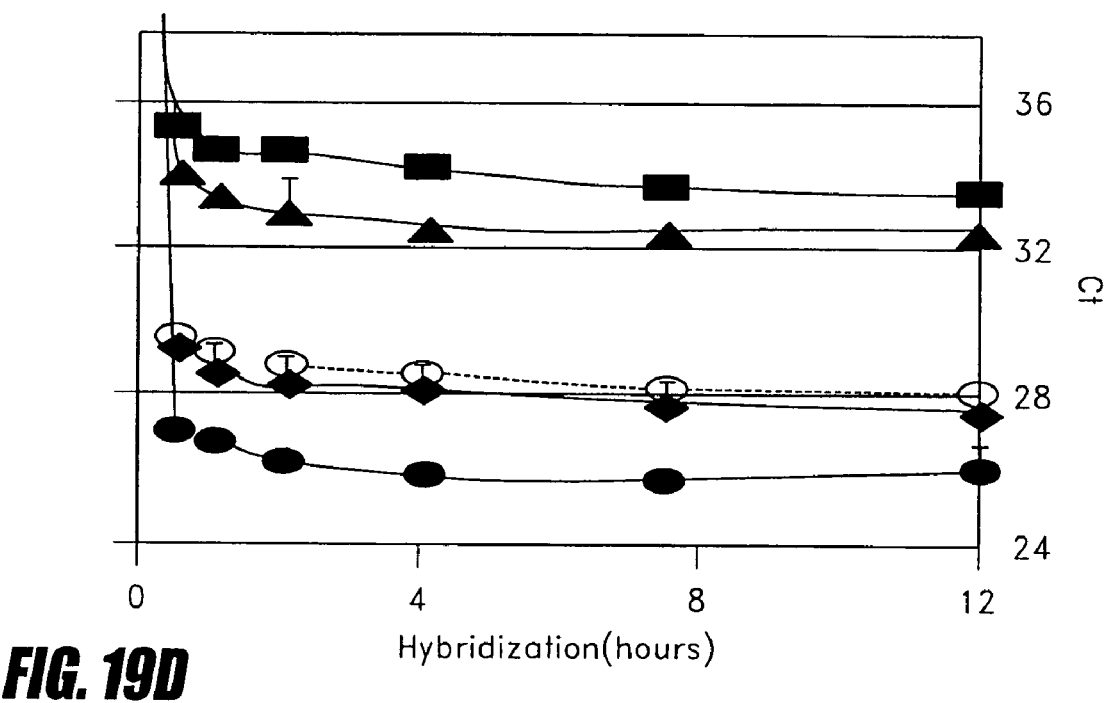
FIG. 19D is a graph showing number of PCR cycles versus hybridization time.

Poly(A)+ mRNA preparation with oligo(dT) solid surface is usually conducted at room temperature. However, the performance varies between 20 and 30° C. (FIG. 19C). When short synthetic RNA was used, the difference between 20 and 23° C. was significant (FIG. 19C). Thus, mRNA preparation step was conducted at 4° C. The length of hybridization was also critical. Some RNAs (standard RNA and FasL) reached a plateau after two hours, whereas others required more than four to eight to stabilize (FIG. 19D). Consequently, the mRNA preparation step was conducted at 4° C. overnight. By switching to this condition, assay-to-assay variation was substantially improved.

Figure 19E:
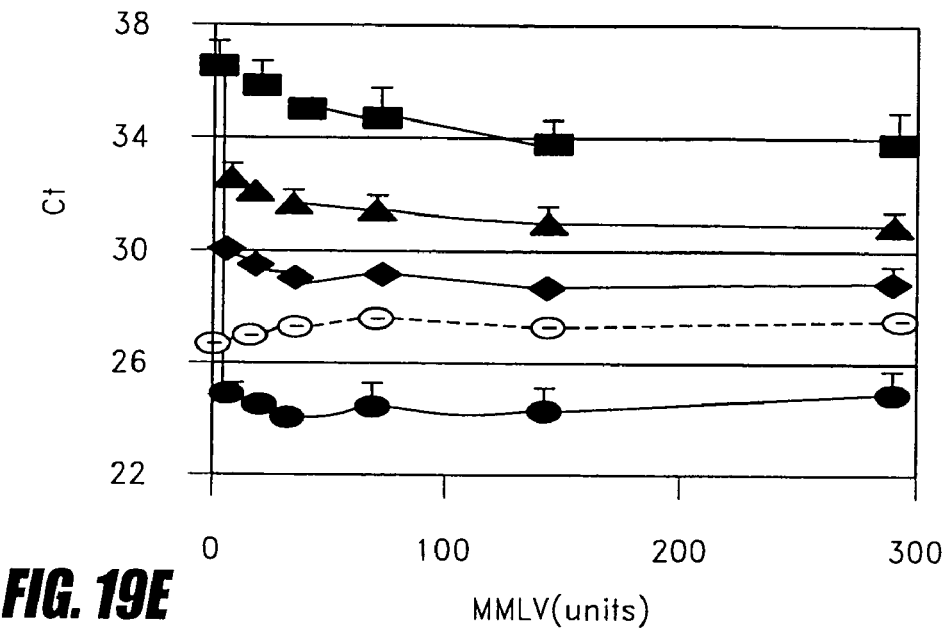
FIG. 19E is a graph showing number of PCR cycles versus units of MMLV.

The cDNA was synthesized without any additional primers (FIG. 18D). Although short synthetic RNA and abundant RNA (CD4) required small amounts of reverse transcriptase, other pieces of RNA required approximately 100 units of MMLV reverse transcriptase to reach to a plateau (FIG. 19E). Interestingly RNaseH$^-$MMLV (Superscript, Invitrogen) exhibited poor performance compared to that of native MMLV in this system. More than 90 min incubation at 37° C. was enough for all species of RNA tested (data not shown).

Figure 19F:
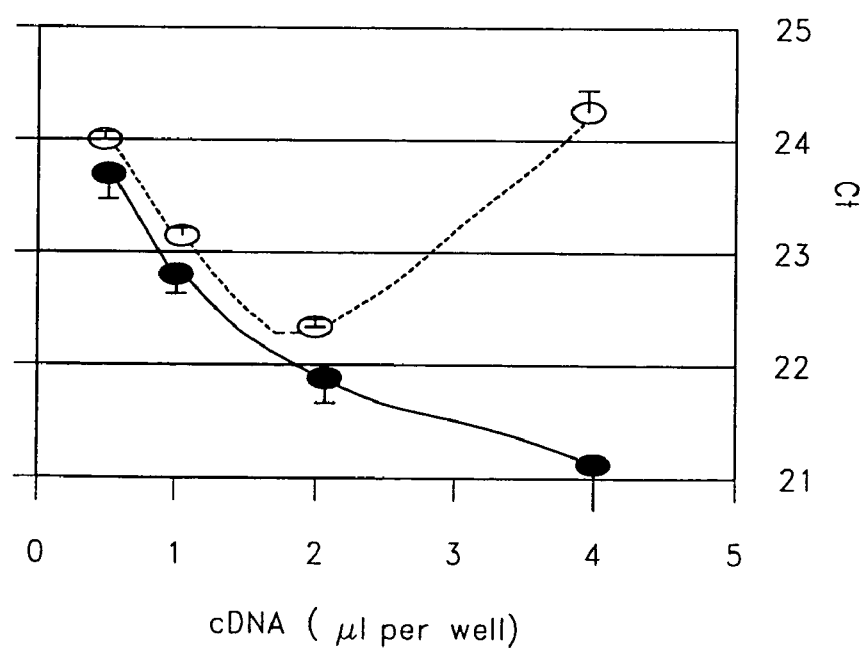
FIG. 19F is a graph showing number of PCR cycles versus µl of cDNA per well.

The cDNA in solution was used directly for subsequent TaqMan real time PCR. The assay becomes sensitive in proportion to the amounts of cDNA transferred to PCR. Commonly available buffers contain dithiothreitol (DTT), which inhibits PCR. Thus, as shown in FIG. 19F, maximal cDNA volume was 2 µl per 10 µl PCR. By removing DTT from buffer, the volume of cDNA increased to 4 µl per 10 µl PCR.

Figure 20B:
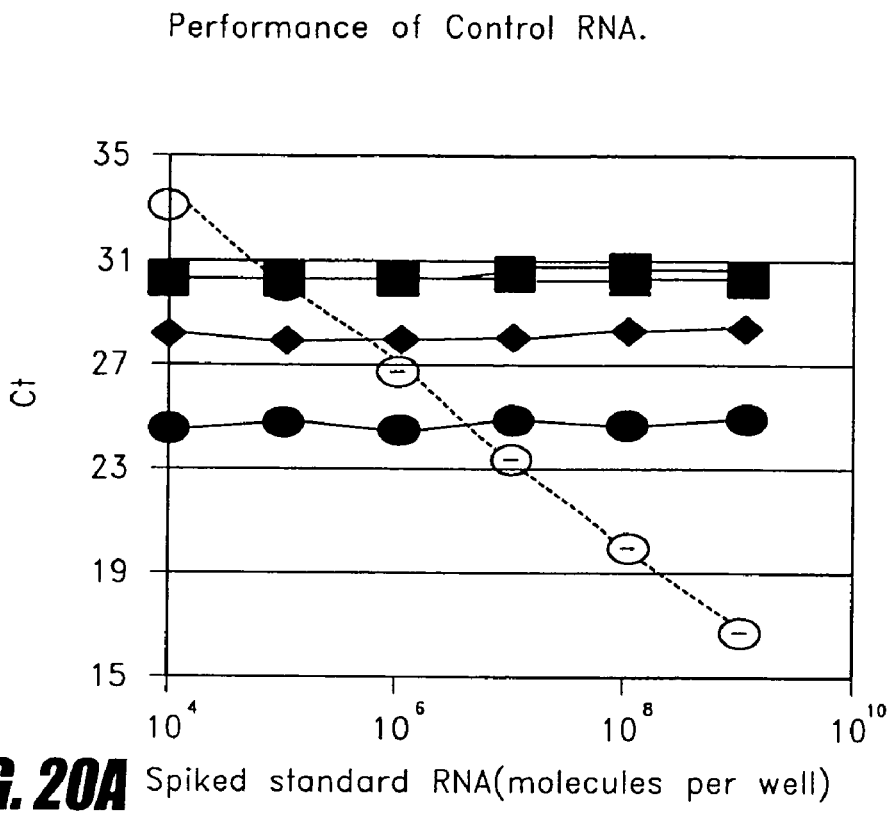
FIG. 20B is a graph showing percent recovery for spiked standard RNA.
Figure 20B:
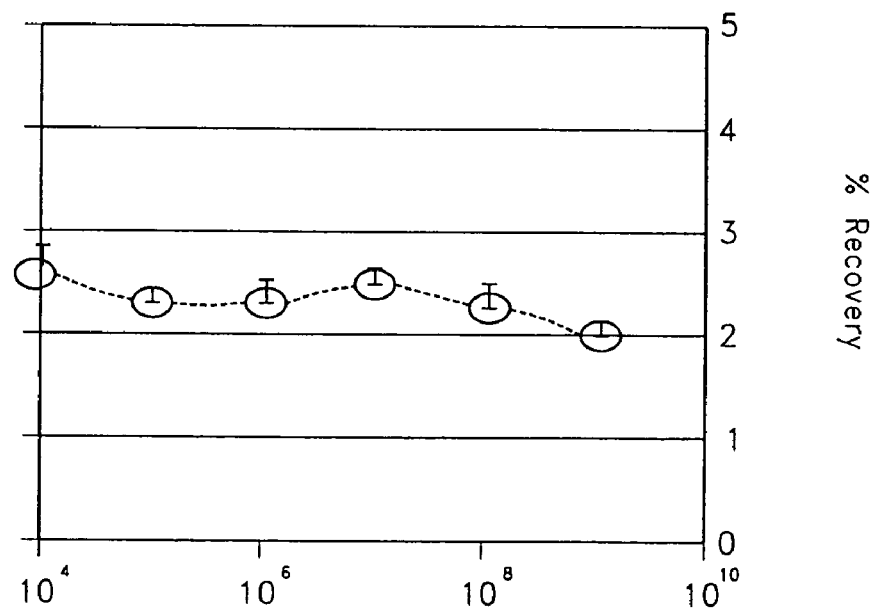

Quantitation. The goal in the quantitation step of this study was to determine total assay efficiency in each sample by using known amounts of spiked standard RNA, which is further used as a denominator to convert PCR results to the quantity of target mRNAs in original samples. The principle relies on two assumptions: that the efficiency is identical between samples of similar mRNA with varying abundancies (dose-independence); and that the efficiency is identical among different mRNA sequences (sequence-independence). In order to validate the first assumption, different amounts of synthetic RNA-standard was added to the lysis buffer, which was exposed to filterplates containing 50 µl of blood. After it was confirmed that standard RNA was not amplified from human blood alone, the recovery of standard RNA was determined by TaqMan PCR. As shown in FIG. 20A (standard RNA (○), CD4 (●), p21 (▲), FasL (◆), and leukotrien C4 synthese mRNA (LTC4S) (■)), dose-dependent recovery of standard RNA was observed at the tested range of $10^4$ to $10^9$ molecules well. Since this range of standard RNA was small enough compared to the amounts of total mRNA existing in 50 µl of blood, the levels of the four other native mRNAs maintained unchanged (FIG. 20A). When the same data were converted to percent recovery, these values all became similar around 2-3% (FIG. 20B). Under the equilibrium conditions of hybridization, the dissociation constant (Kd) was calculated as followed:

$$Kd=[RNA]\times[oligo(dT)]/[RNA:oligo(dT)]$$

where [RNA] and [oligo(dT)] represent the concentrations of unbound states of RNA and oligo(dT), respectively, and [RNA:oligo(dT)] represents the concentrations of hybridized RNA with oligo(dT). This means that the Kd is maintained as a constant value in this system, and [RNA:oligo(dT)] changes depending on the amounts of applied RNA (FIG. 20A). In fact, [RNA:oligo(dT)] was increased in proportion to the amounts of applied RNA, when hybridized whole RNA was directly measured by Yoyo-1 nucleic acid dye. These data also suggest that the percent recovery derived from one concentration of standard RNA can be applicable to any concentration of mRNA within the same samples.

Figure 20C:
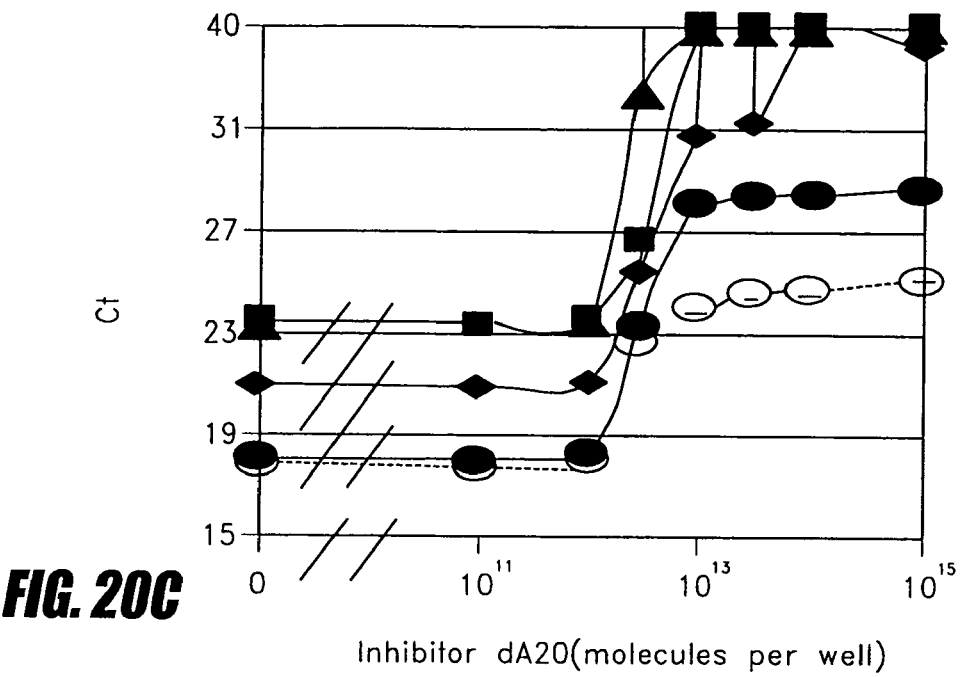
FIG. 20C is a graph showing Ct values for inhibitor dA20.
Figure 20D:
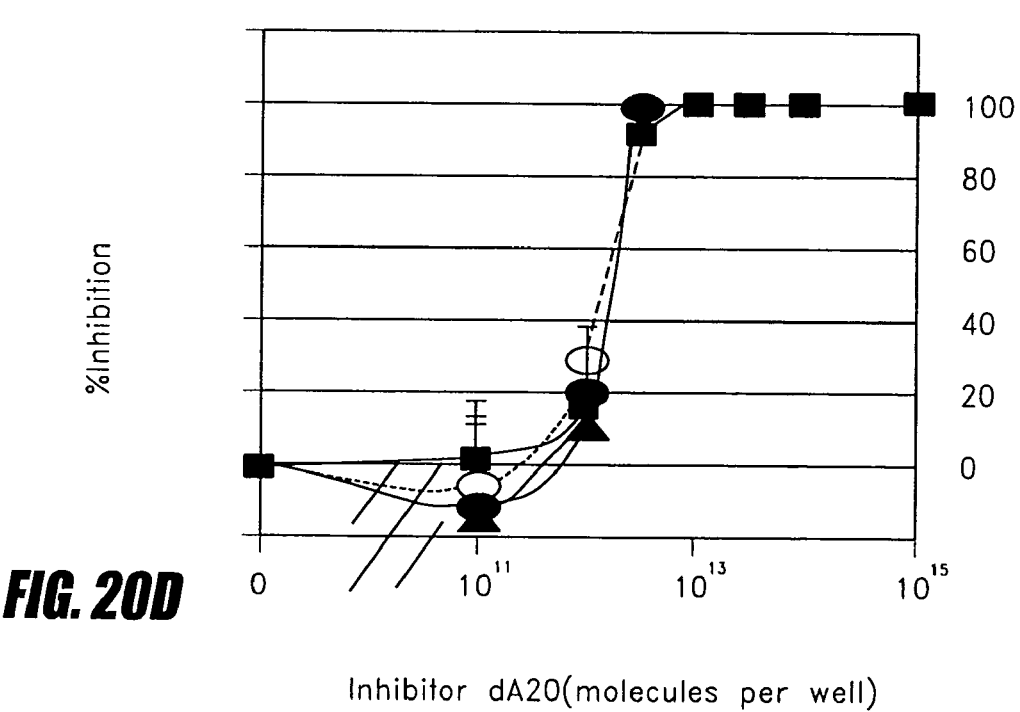
FIG. 20D is a graph showing percent inhibition for inhibitor dA20.

For the second assumption, hybridization was carried out with or without oligo(dA) as a competitive inhibitor. As shown in FIG. 20C, the Ct values of all five target RNAs were significantly inhibited by oligo(dA) at more than $3\times10^{12}$ molecules per well, although the expression levels of these RNAs were all different. Interestingly, when the same data were transformed to the percent inhibition, all five RNAs showed almost identical inhibition curves with an $IC_{50}$ around $3\times10^{12}$-$10^{13}$ molecules per well (FIG. 20D). This indicates that the system is poly(A)-specific, and sequence-independent. As shown in FIG. 20C, some non-specific activities remained even after $10^{15}$ molecules of oligo(dA) were applied (standard RNA and CD4). However, as shown in FIG. 20D, these non-specific activities were negligible, when the Ct values (log scale) were converted to the number of molecules (linear scale). Thus, non-poly(A) sequences do not appear to play major role in this system. Because FIGS. 20A-D were the sum of whole processes of mRNA quantitation, these data suggest that the total assay efficiency of any target gene is identical to that of spiked standard RNA. This is unique to poly(A)$^+$ RNA, because substantial variation exists between long and short RNA in conventional total RNA purification methods (data not shown).

Figure 20E:
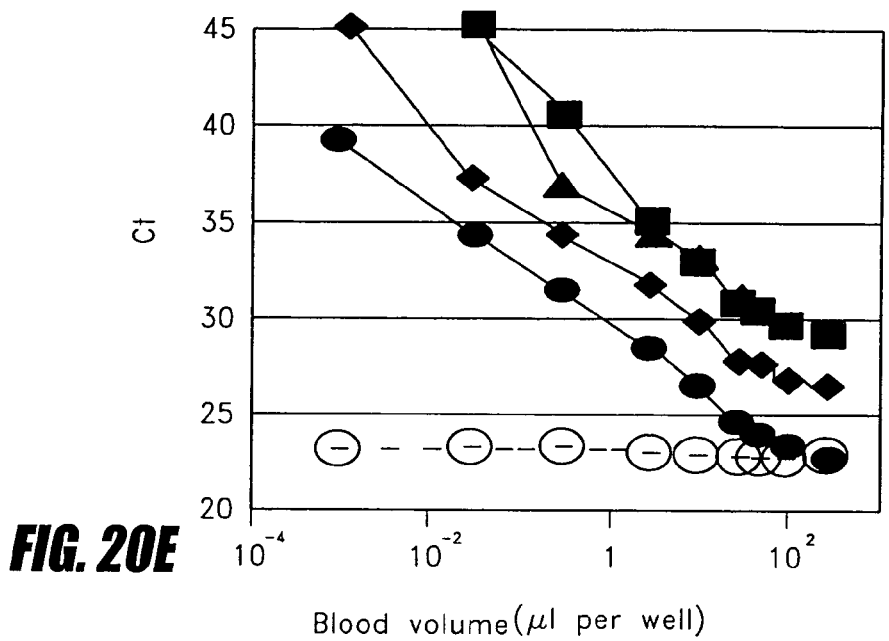
FIG. 20E is a graph showing Ct values per µl of blood.
Figure 20F:
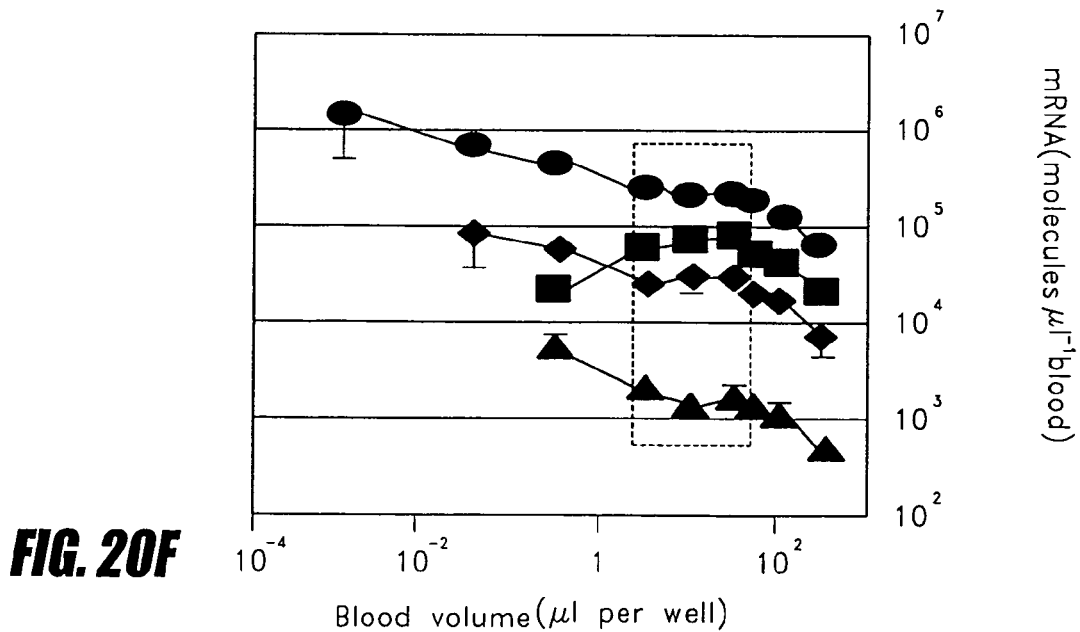
FIG. 20F is a graph showing mRNA recovery per µl of blood.

The next step was to convert the amounts of RNA in each well to the amounts of RNA per µl of blood. As shown in FIG. 20E, the Ct values of four native mRNAs were decreased almost linearly, depending on the volume of blood applied. Abundant mRNA such as CD4 was detectable from even 0.001 µl of blood (1:$10^5$ dilution, 100 µl per well) (FIG. 20E). Since the amount of standard RNA in lysis buffer was identical, the recovery of standard RNA was unchanged even when the blood volume varied widely FIG. 20E. The Ct values reached a plateau at more than 100 µl blood per well (FIG. 20E), suggesting increased leakage of leukocytes from filterplates. Once the same data were transformed to amounts of µl$^{-1}$ blood, the values were consistent between 3 and 50 µl blood per well (FIG. 20F), which was true for all four native mRNAs (FIG. 20F).

The quantitation also relies on two independent absolute values: the quantity of applied standard RNA, and the quantity of standard DNA templates in TaqMan PCR. To ensure the purity of the standard RNA products, RNA oligonucleotides were used in this project. While the synthesis of RNA oligonucleotides with a length of 100 bases long can be difficult to achieve, such a length is desirable because RNA oligonucleotides preferably comprises two primer sites, a TaqMan probe site, and a poly(A) tail. Synthetic RNA in the present study was synthesized by Dharmacon with a purity of 86% by HPLC analysis. HPLC-purified DNA oligonucleotides were also used as templates for TaqMan PCR because the slope of the amplification curve (showing PCR efficiency) was identical between oligonucleotides and cDNA. A standard curve was generated with $10^6$-10 molecules of oligonucleotides per well. A problem occurred during $10^6$ to $10^{12}$ times dilution of µM concentrations of stock solution. When TE or water was used as a diluent, the standard curve varied widely, particularly with less than $10^3$ molecules per well. After switching to nuclease-free water containing 0.1% tween-20, this problem was completely eliminated.

Figures 21A, 21B, 21C, 21D, 21E:
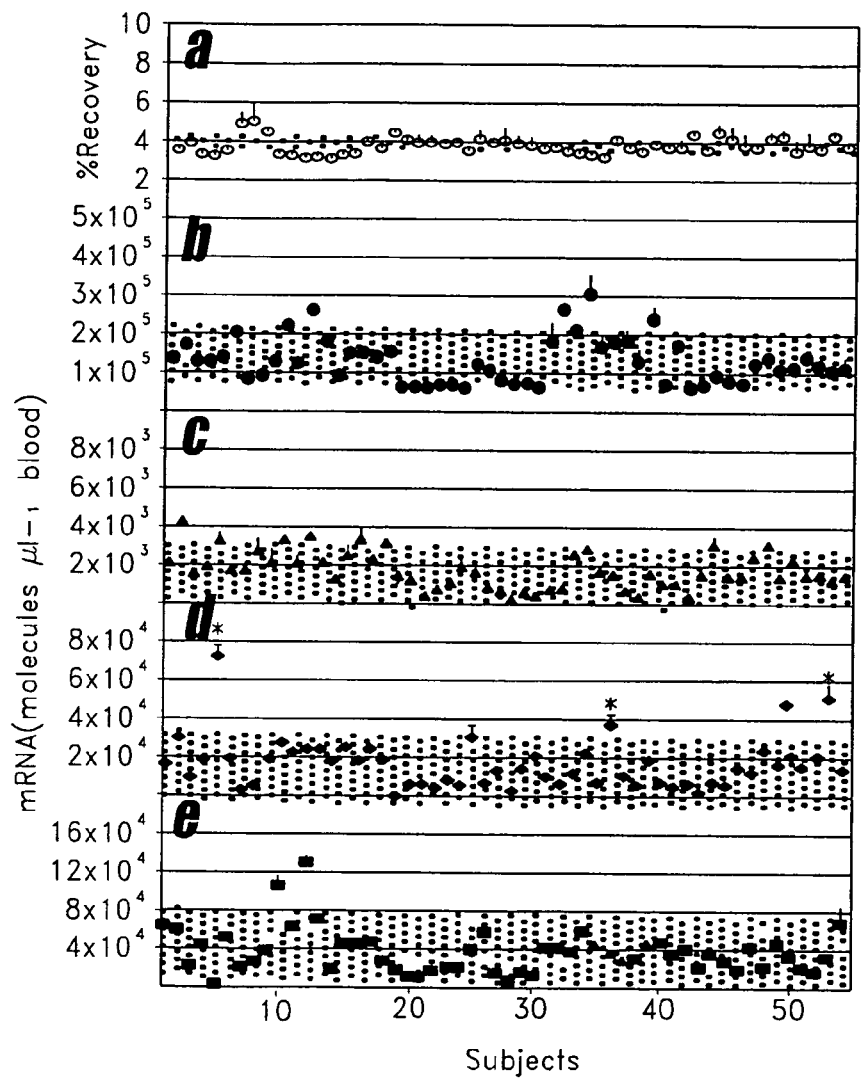
FIG. 21A is a graph showing percent recovery of standard RNA among various subjects.
FIG. 21B is a graph showing CD4 mRNA per µl of blood recovered among various subjects.
FIG. 21C is a graph showing p21 mRNA per µl of blood recovered among various subjects.
FIG. 21D is a graph showing FasL mRNA per µl of blood recovered among various subjects.
FIG. 21E is a graph showing LTC4S mRNA per µl of blood recovered among various subjects.

Determining Normal Values. In order to determine the control values of mRNA per μl of blood in healthy subjects, the levels of CD4, p21, FasL, and LTC4S were measured from 52 individuals (54 data points, with one individual repeated three times) over two months, through 15 different experiments. Each data point was derived from three aliquots of 50 μl whole blood. As shown in FIG. 21A, the recovery of standard RNA was 3.56±0.49% (CV=13.7%). Although this CV value is much larger than a conventional immunoassay, it is acceptable because it uses PCR, where one cycle difference represents a doubling in product quantity. Using the values of standard RNA recovery, the data of each mRNA were successfully converted to the number of molecules per μl of blood, rather than relying on pico moles or femto moles.

As shown in FIGS. 21B-E (standard RNA (○), CD4 (●), p21 (▲), FasL (◆), and leukotrien C4 synthese mRNA (LTC4S) (■)), control levels of CD4, p21, FasL, and LTC4S mRNA were 100,772±59,184 (CV=58.7%), 1,692±858 (CV=50.7%), 17,841±12,190 (CV=68.3%), and 42,058±22,521 (CV=53.5%) molecules per μl of blood, respectively. Fifty percent CV means that the normal values reside within one Ct in TaqMan PCR. Interestingly, when the mean±1 s.d. values were blanketed in each figure, some individuals expressed high values (FIGS. 21B-E). One individual who expressed high FasL mRNA levels was reproduced three times (FIG. 21D). Determination of normal values of mRNA, combined with low CV values and standardization obtainable by preferred embodiments of the present invention, can be used in assays for the detection of various diseases known to those skilled in the art.

Figure 22A:
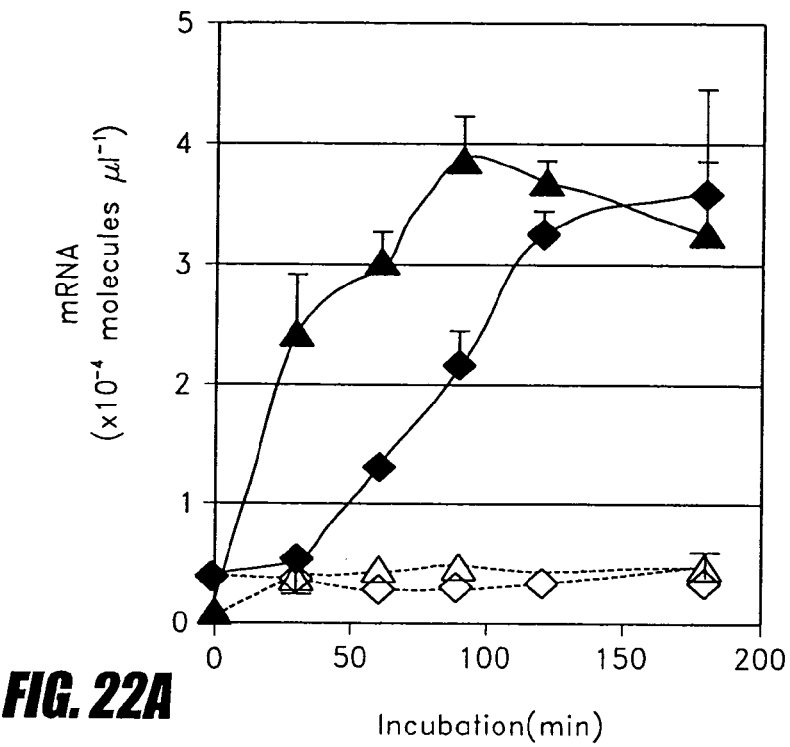
In FIGS. 22A-H, Δ shows p21 mRNA for the control stimulation, ▲ shows p21 mRNA for the PMA+CaI stimulation, ◇ shows FasL mRNA for the control stimulation, and ◆ shows FasL mRNA for the PMA+CaI stimulation.
Figure 22B:
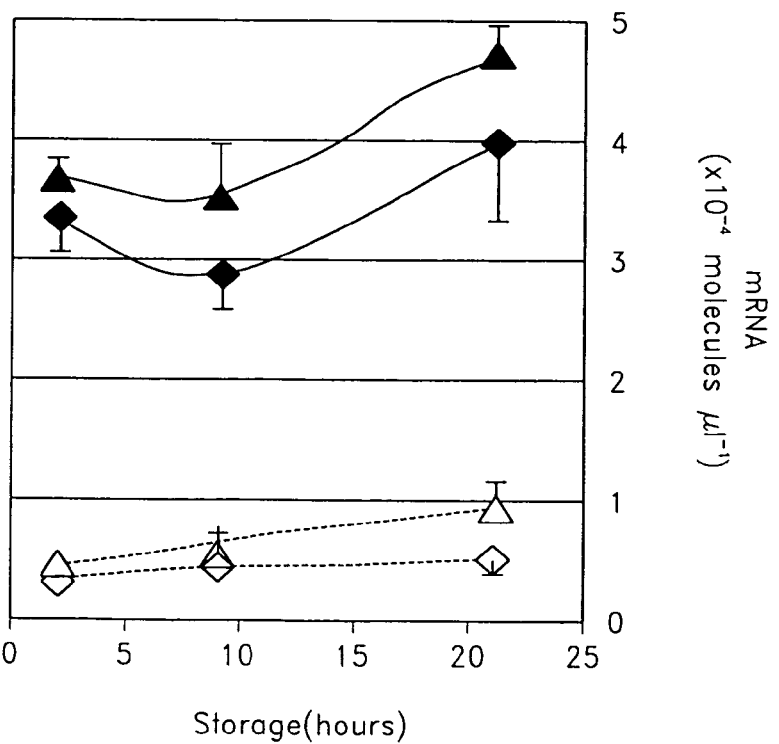

In vitro Responsiveness. In order to assess leukocyte responsiveness against phorbol 12-myristate 13-acetate (PMA) and calcium ionophore A23187 (CaI) (Sigma) as a model system, the levels of p21 and FasL mRNA was quantitated (FIG. 22). In other preferred embodiments, various types of mRNA can be analyzed in response to stimulation by various bioactive agents, including but not limited to, for example: radiation, ultraviolet, oxidative stress, ozone, temperature, mechanical stress, chemicals, peptides, hormones, proteins, antigens, antibodies, drugs, small molecule compounds, toxic materials, environmental stimuli, cell-cell communications, infectious agents, and allergens. Since the system used heparinized whole blood, rather than an isolated leukocyte suspension in artificial solution, the results reflected physiologically accurate conditions. In FIGS. 22A-H, Δ shows p21 mRNA for the control stimulation, ▲ shows p21 mRNA for the PMA+CaI stimulation, ◇ shows FasL mRNA for the control stimulation, and ◆ shows FasL mRNA for the PMA+CaI stimulation. As shown in FIG. 22A, both p21 and FasL mRNA levels increased rapidly upon stimulation of PMA and CaI, and reached a plateau after 90-120 minutes with approximately a ten-fold increase. The increases in p21 were much faster than those of FasL (FIG. 22A). The levels of p21 were also increased slightly by incubation at 37° C. without any stimulation, whereas FasL remained unchanged (FIG. 22A). Interestingly, the responsiveness was preserved even when heparinized whole blood was stored at 4° C. for 21 hours (FIG. 22B), which provides wide flexibility for functional molecular analysis.

Figure 22C:
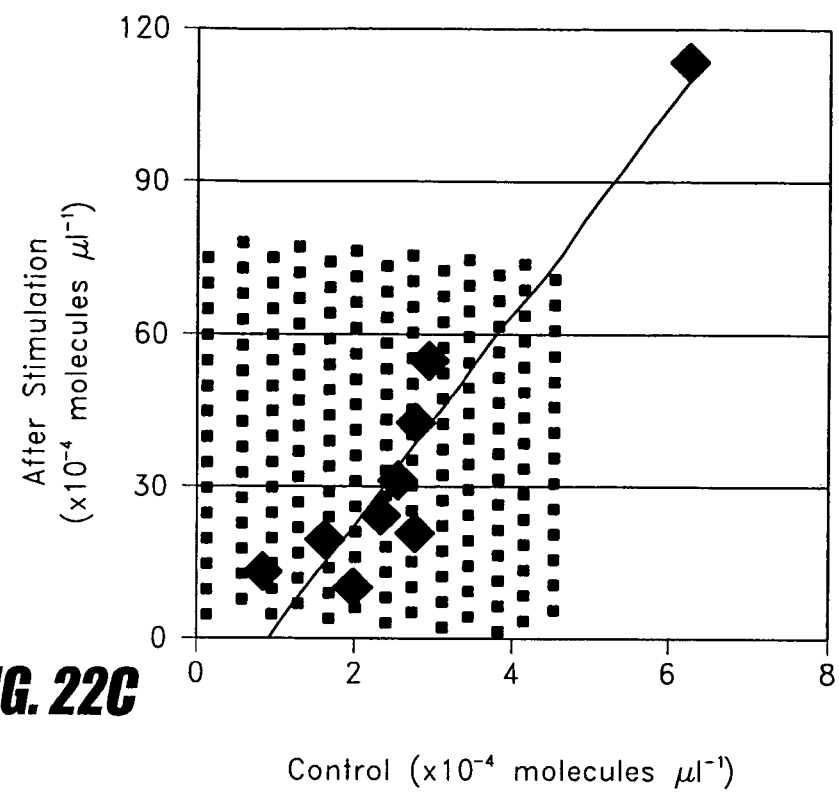
Figure 22D:
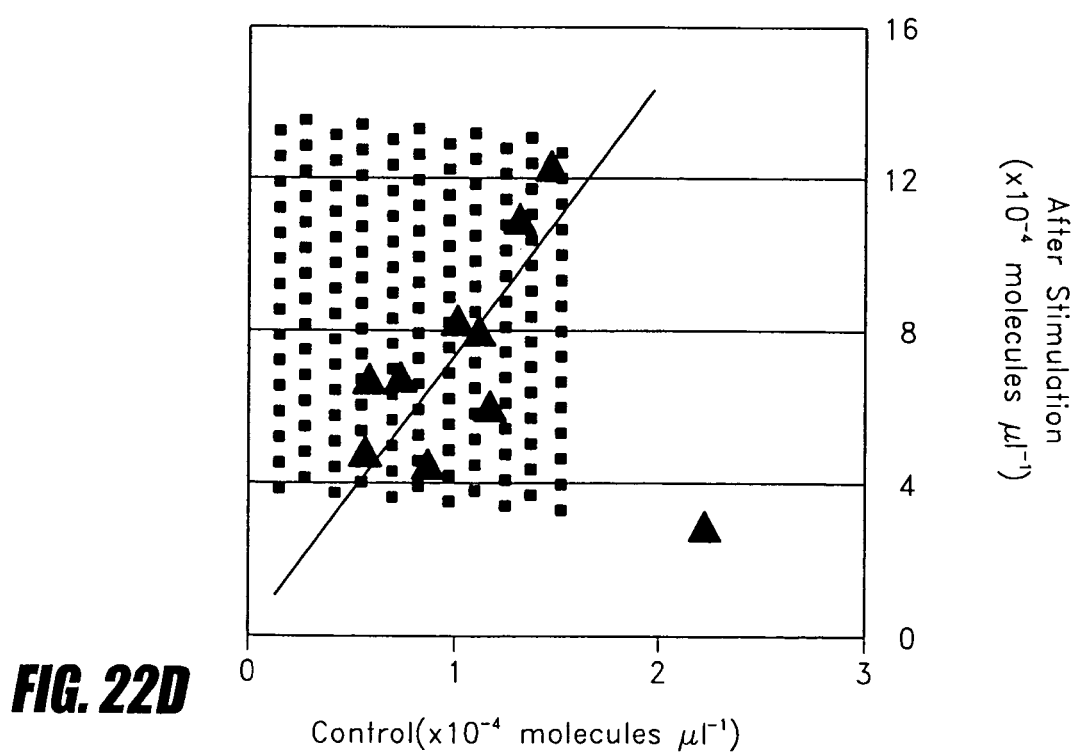
Figure 22E:
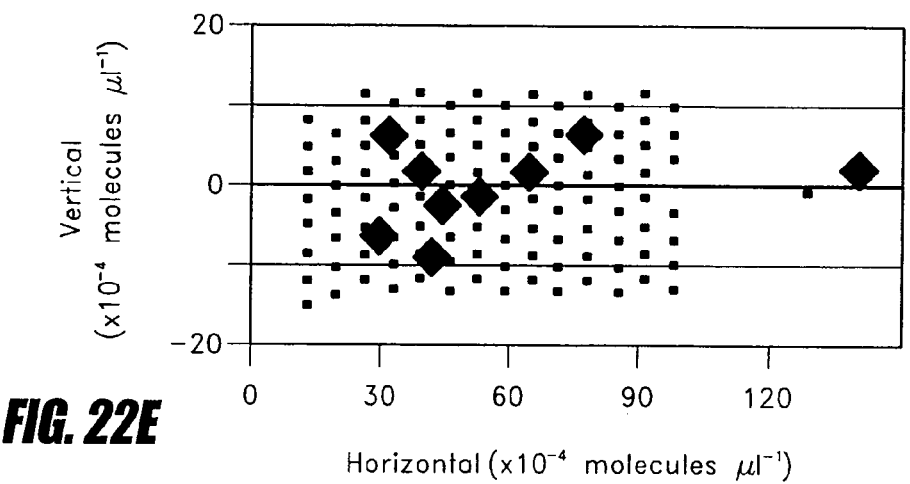
Figure 22F:
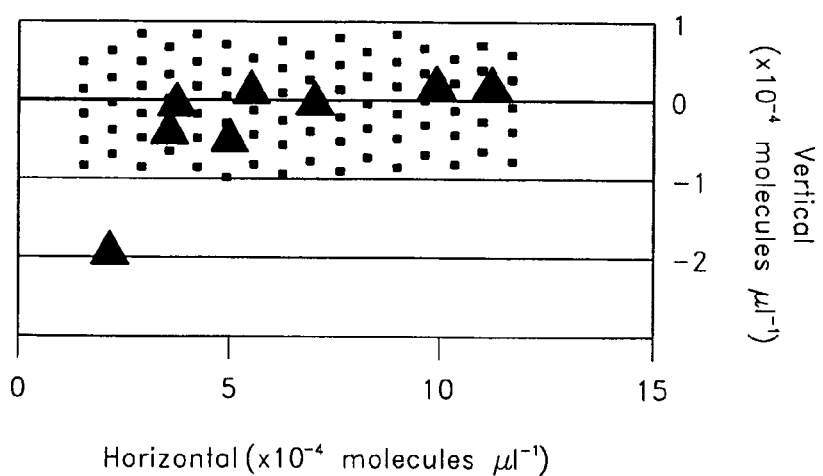
Figure 22G:
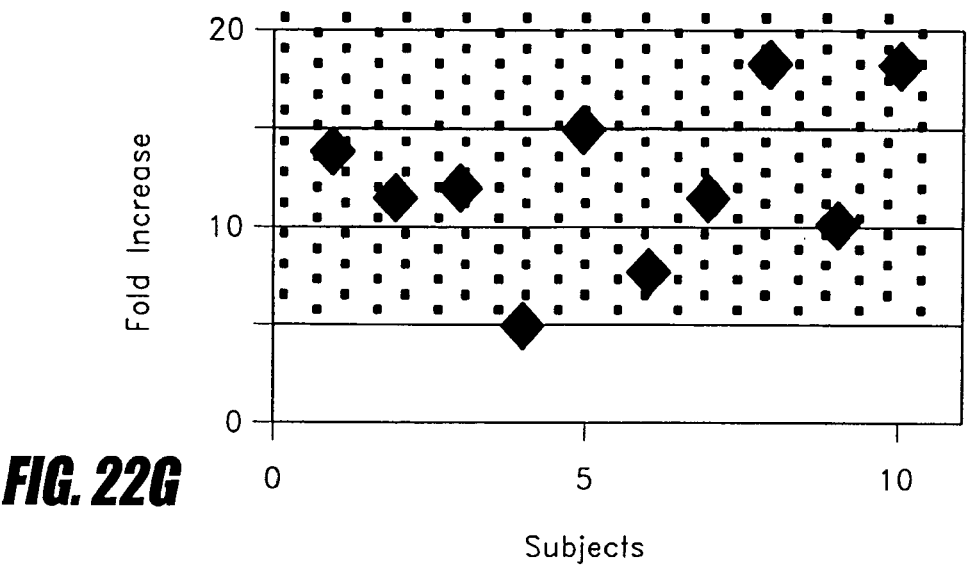
Figure 22H:
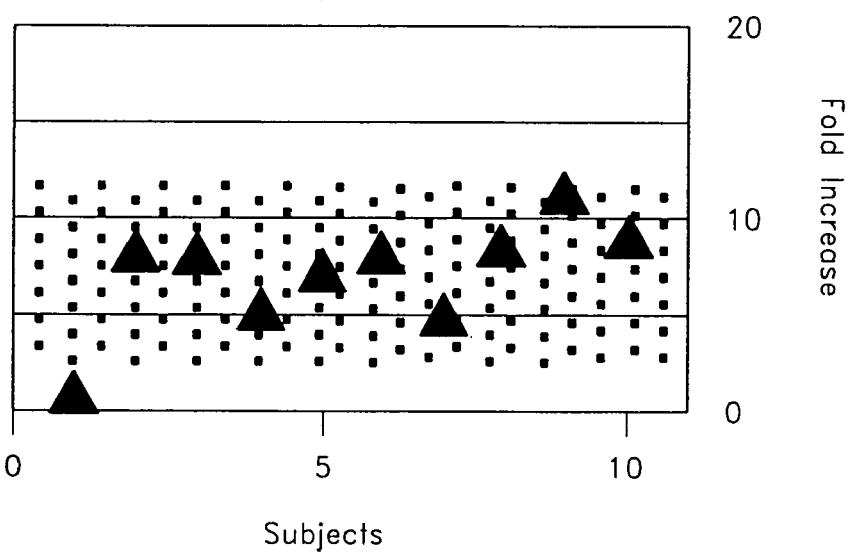

In analyzing up- or down-regulation of mRNA expression, fold-increase is a commonly used parameter. However, as shown in FIGS. 22C-D, the amounts of p21 and FasL mRNA induced after PMA-CaI stimulation increased linearly depending on the amounts of basal levels of mRNA. Thus, the fold-increase measurement was not capable of identifying non-ordinary samples that resided on the regression line (FIG. 22G), even when the sample was more than two standard deviations apart from the normal population (FIG. 22C). The fold-increase measurement identified an abnormal sample (FIG. 22H) that resided away from the regression line (FIG. 22D). The two dimensional graphs of FIGS. 22C-D clearly distinguished ordinary and non-ordinary samples in both cases. In FIGS. 22C-H, each data point is the mean from triplicate determinations. In order to make the graph simple, the standard deviation was not shown. However, because the blanket areas with mean±2 s.d. in both X- and Y-axes (FIGS. 22C-D) contained open spaces in the upper left and lower right corners, non-ordinary samples in these corners were difficult to identify. By rotating the X-axis to the regression line (FIGS. 22E-F), the size of the blanketed areas were minimized. These graphs (FIGS. 22E-F) provide a better way to detect non-ordinary samples out of the normal population.

What is claimed is:

1. A method of obtaining mRNA from a leukocyte lysate comprising:
   obtaining whole blood;
   preparing a plurality of sample wells, each of the sample wells comprising a filter that traps leukocytes in the filter and allows erythrocytes and blood components other than leukocytes in the whole blood to be removed from the filter;
   adding an anticoagulant to the whole blood;
   adding the whole blood to the sample wells;
   removing erythrocytes and blood components other than leukocytes in the whole blood from the filter;
   lysing the leukocytes in the samples wells by applying lysis buffer comprising a guanidinium thiocyanate at a concentration in the range of about 1.4M to 1.75M into the sample wells and obtaining a leukocyte lysate comprising mRNA in each of the sample wells;
   transferring said leukocyte lysate from each of the sample wells into its corresponding mRNA capture zone in which oligo(dT) is immobilized; and
   obtaining said mRNA from said leukocyte lysate by annealing poly-A mRNA in the leukocyte lysate to the oligo(dT).

2. The method of claim 1, wherein the leukocytes are located on the filter at the time they are lysed.

3. The method of claim 2, wherein the lysis buffer comprises a detergent.

4. The method of claim 3, wherein the detergent is Triton X-100, Tween-20, SDS (sodium dodecyl sulfate), sarcosyl, or deoxycholic acid.

5. The method of claim 2, wherein the lysis buffer further comprises an additional ribonuclease inhibitor.

6. The method of claim 1, further comprising assaying for the presence or quantity of one or more RNAs in the lysate.

7. The method of claim 6, wherein said assaying step comprises a Northern blot, RNase protection assay, hybridization reaction, microarray analysis, or reverse transcriptase-polymerase chain reaction analysis.

8. The method of claim 7, wherein said reverse transcriptase-polymerase chain reaction analysis is real-time RT-PCR or endpoint RT-PCR.

9. The method of claim 1, wherein the oligo(dT) is immobilized on a plate comprising the plurality of sample wells and the transferring step is performed by vacuum aspiration.

10. The method of claim 1, wherein the oligo(dT) is immobilized on a plate comprising the plurality of sample wells and the transferring step is performed by centrifugation.

11. A method of obtaining mRNA from a leukocyte lysate comprising:
    obtaining whole blood;
    preparing a plurality of sample wells, each of the sample wells comprising a filter that traps leukocytes in the filter and allows erythrocytes and blood components other than leukocytes in the whole blood to be removed from the filter;
    adding an anticoagulant to the whole blood;
    adding the whole blood to the sample wells;
    removing erythrocytes and blood components other than leukocytes in the whole blood from the filter; and
    lysing the leukocytes in the samples wells by applying lysis buffer comprising guanidine thiocyanate at a concentration in the range of about 1.4M to 1.75M into the sample wells and obtaining a leukocyte lysate comprising mRNA;
    extracting the mRNA from the leukocyte lysate and obtaining extracted mRNA;
    transferring said extracted mRNA into an mRNA capture zone in which oligo(dT) is immobilized; and
    obtaining said mRNA from said leukocyte lysate by annealing said mRNA to the oligo(dT).

12. The method of claim 11, wherein the extraction is performed via an organic extraction.

13. The method of claim 12, wherein the organic extraction is a phenol/chloroform extraction.

14. The method of claim 9, wherein said extracting the mRNA from the leukocyte lysate comprises extracting the lysate with an organic solution, forming organic and aqueous phases; separating the organic and aqueous phases; and isolating the mRNA from the aqueous phase.

* * * * *

SEQUENCE LISTING

<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide primer sequence

<400> SEQUENCE: 1
gggtgctgtg cttctgtgaa c                                             21

<210> SEQ ID NO 2
<211> LENGTH: 63
<212> TYPE: DNA
<213> ORGANISM: Artificial Sequence
<220> FEATURE:
<223> OTHER INFORMATION: Synthetic oligonucleotide sequence

<400> SEQUENCE: 2

```
gcccctcac tcccaaattc caaggcccag ccctcacaca ttgttcacag aagcacagca    60
ccc                                                                 63

<210> SEQ ID NO 3
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 3
gtaatacgac tcactatagg gggacagccc cctcactccc aaa                     43

<210> SEQ ID NO 4
<211> LENGTH: 67
<212> TYPE: DNA
<213> ORGANISM: Artificial Sequence
<220> FEATURE:
<223> OTHER INFORMATION: Synthetic oligonucleotide  sequence

<400> SEQUENCE: 4
gaagcgtgtg tcactgtgtg tttccaaggc ccagccctca cacattgttc acagaagcac   60
agcaccc                                                             67

<210> SEQ ID NO 5
<211> LENGTH: 47
<212> TYPE: DNA
<213> ORGANISM: Artificial Sequence
<220> FEATURE:
<223> OTHER INFORMATION: Synthetic oligonucleotide primer sequence

<400> SEQUENCE: 5
gtaatacgac tcactatagg gggacggaag cgtgtgtcac tgtgtgt                 47

<210> SEQ ID NO 6
<211> LENGTH: 46
<212> TYPE: DNA
<213> ORGANISM: Artificial Sequence
<220> FEATURE:
<223> OTHER INFORMATION: Synthetic oligonucleotide primer sequence

<400> SEQUENCE: 6
gtaatacgac tcactatagg gggacgcatt ccgctgacca tcaata                  46

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide  sequence

<400> SEQUENCE: 7
tccaacgagc ggcttcac                                                 18

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide primer sequence

<400> SEQUENCE: 8
aaatgccaca cggctctca                                                19
```

```
<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide primer sequence

<400> SEQUENCE: 9
caagtgtctt cgtgtcgtgg g                                              21

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide primer sequence

<400> SEQUENCE: 10 agcccctca ctcccaaa                                                   18

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide primer sequence

<400> SEQUENCE: 11 agcccctca ctcccaaa                                                   18

<210> SEQ ID NO 12
<211> LENGTH: 33
<212> TYPE: DNA
<213> ORGANISM: Artificial Sequence
<220> FEATURE:
<223> OTHER INFORMATION: Synthetic oligonucleotide probe sequence

<400> SEQUENCE: 12
cagtggctag tggtgggtac tcaatgtgta ctt                                 33

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide probe sequence

<400> SEQUENCE: 13
ccaaggccca gccctcacac a                                              21

<210> SEQ ID NO 14
<211> LENGTH: 89
<212> TYPE: DNA
<213> ORGANISM: Artificial Sequence
<220> FEATURE:
<223> OTHER INFORMATION: Synthetic oligonucleotide  sequence

<400> SEQUENCE: 14
cagggacaaa tgccacacgg ctctcaccag tggctagtgg tgggtactca atgtgtactt    60
ttgggttcac agaagcacag cacccaggg                                      89

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide primer sequence
```

-continued

```
<400> SEQUENCE: 15
ccactggatt taagcagagt tcaa                                              24

<210> SEQ ID NO 16
<211> LENGTH: 18
<212> TYPE: DNA
<213> ORGANISM: Artificial Sequence
<220> FEATURE:
<223> OTHER INFORMATION: Synthetic oligonucleotide primer sequence

<400> SEQUENCE: 16
tccaacgagc ggcttcac                                                     18

<210> SEQ ID NO 17
<211> LENGTH: 26
<212> TYPE: DNA
<213> ORGANISM: Artificial Sequence
<220> FEATURE:
<223> OTHER INFORMATION: Synthetic oligonucleotide probe sequence

<400> SEQUENCE: 17
cagcggccag tagcatctga ctttga                                            26
```